United States Patent
Bongalon

(10) Patent No.: US 12,300,374 B2
(45) Date of Patent: May 13, 2025

(54) OPERATION PROFILE SYSTEMS AND METHODS FOR A COMPUTER-ASSISTED SURGICAL SYSTEM

(71) Applicant: Intuitive Surgical Operations, Inc., Sunnyvale, CA (US)

(72) Inventor: Benjamin T. Bongalon, Daly City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 511 days.

(21) Appl. No.: 17/611,410

(22) PCT Filed: Jun. 3, 2020

(86) PCT No.: PCT/US2020/035858
§ 371 (c)(1),
(2) Date: Nov. 15, 2021

(87) PCT Pub. No.: WO2020/247451
PCT Pub. Date: Dec. 10, 2020

(65) Prior Publication Data
US 2022/0208335 A1    Jun. 30, 2022

Related U.S. Application Data

(60) Provisional application No. 62/857,439, filed on Jun. 5, 2019.

(51) Int. Cl.
*G16H 20/40* (2018.01)
*A61B 34/00* (2016.01)
(Continued)

(52) U.S. Cl.
CPC .............. *G16H 20/40* (2018.01); *A61B 34/20* (2016.02); *A61B 34/25* (2016.02); *A61B 34/35* (2016.02);
(Continued)

(58) Field of Classification Search
None
See application file for complete search history.

(56) References Cited

U.S. PATENT DOCUMENTS

| 2016/0210412 A1* | 7/2016 | Zellner | G16H 50/50 |
| 2016/0331474 A1* | 11/2016 | Lacal | B25J 9/1664 |
| 2020/0078105 A1* | 3/2020 | Itkowitz | A61G 13/02 |

FOREIGN PATENT DOCUMENTS

| EP | 2778998 A1 | 9/2014 |
| WO | WO-2018031861 A1 | 2/2018 |

OTHER PUBLICATIONS

Sugiyama T, Lama S, Gan LS. Forces of Tool-Tissue Interaction to Assess Surgical Skill Level. JAMA Surg. Mar. 1, 2018;153(3):234-242. doi: 10.1001/jamasurg.2017.4516. Erratum in: JAMA Surg. Mar. 1, 2018;153(3):292. doi: 10.1001/jamasurg.2017.5835. PMID: 29141073; PMCID: PMC5885969. (Year: 2018).*

(Continued)

*Primary Examiner* — Katherine Kolosowski-Gager

(57) ABSTRACT

An operation profile system may collect surgical session data representative of surgical procedure operations performed during a surgical session and may access operation pattern data representative of multiple historical patterns of surgical procedure operations. The system may identify, based on the operation pattern data and the surgical session data, a first historical pattern included in the multiple historical patterns of surgical procedure operations and that matches a first collected pattern from the surgical procedure operations. The system may provide, for use during the surgical session, a first operation profile associated with the first historical pattern that matches the first collected pattern.

20 Claims, 12 Drawing Sheets

(51) Int. Cl.
    *A61B 34/20*     (2016.01)
    *A61B 34/35*     (2016.01)
    *A61B 34/37*     (2016.01)
    *A61B 90/00*     (2016.01)
    *G16H 40/63*     (2018.01)
    *G16H 40/67*     (2018.01)
    *G16H 50/70*     (2018.01)

(52) U.S. Cl.
    CPC .............. *A61B 34/37* (2016.02); *A61B 90/37* (2016.02); *G16H 40/63* (2018.01); *G16H 40/67* (2018.01); *G16H 50/70* (2018.01); *A61B 2034/254* (2016.02); *A61B 2034/256* (2016.02); *A61B 2034/258* (2016.02)

(56) References Cited

OTHER PUBLICATIONS

International Preliminary Report on Patentability for Application No. PCT/US2020/035858 mailed on Dec. 16, 2021, 8 pages.
International Search Report and Written Opinion for Application No. PCT/US2020/035858, mailed Aug. 27, 2020, 10 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

OPERATION PROFILE SYSTEMS AND METHODS FOR A COMPUTER-ASSISTED SURGICAL SYSTEM

RELATED APPLICATIONS

The present application is a U.S. National Stage Application under 35 U.S.C. § 371 of International Application No. PCT/US2020/035858, filed on Jun. 3, 2020, which claims priority to U.S. Provisional Patent Application No. 62/857,439, filed on Jun. 5, 2019, the contents of which are hereby incorporated by reference in their entirety.

BACKGROUND INFORMATION

During a computer-assisted surgical procedure, such as a minimally invasive surgical procedure, a surgeon may interact with a computer-assisted surgical system to control teleoperated surgical instruments to perform the surgical procedure on a patient. Other surgical team members may also interact with the computer-assisted surgical system to assist with the surgical procedure. However, the computer-assisted surgical system does not provide the surgical team members with timely, task-relevant automated support that can help them perform the surgical procedure more efficiently, more ergonomically, and with better situational awareness.

SUMMARY

The following description presents a simplified summary of one or more aspects of the methods and systems described herein in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects of the methods and systems described herein in a simplified form as a prelude to the more detailed description that is presented below.

An exemplary system may include a memory storing instructions and a processor communicatively coupled to the memory and configured to execute the instructions to collect surgical session data representative of surgical procedure operations performed during a surgical session; access operation pattern data representative of multiple historical patterns of surgical procedure operations; identify, based on the operation pattern data and the surgical session data, a first historical pattern included in the multiple historical patterns of surgical procedure operations and that matches a first collected pattern from the surgical procedure operations; and provide, for use during the surgical session, a first operation profile associated with the first historical pattern that matches the first collected pattern.

An exemplary method may include collecting, by an operation profile system, surgical session data representative of surgical procedure operations performed during a surgical session; accessing, by the operation profile system, operation pattern data representative of multiple historical patterns of surgical procedure operations; identifying, by the operation profile system based on the operation pattern data and the surgical session data, a first historical pattern included in the multiple historical patterns of surgical procedure operations and that matches a first collected pattern from the surgical procedure operations; and providing, by the operation profile system for use during the surgical session, a first operation profile associated with the first historical pattern that matches the first collected pattern.

An exemplary non-transitory computer-readable medium stores instructions that, when executed, direct at least one processor of a computing device to collect surgical session data representative of operations of a computer-assisted surgical system during a surgical session; access operation pattern data representative of multiple distinct historical patterns of operations of one or more computer-assisted surgical systems; identify a distinct set of operation pattern data representative of a distinct historical pattern of operations that is selected from among the multiple distinct historical patterns of operations and that best matches at least a portion of the surgical session data; and provide, for use by the computer-assisted surgical system during the surgical session, an operation profile associated with the distinct set of operation pattern data.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
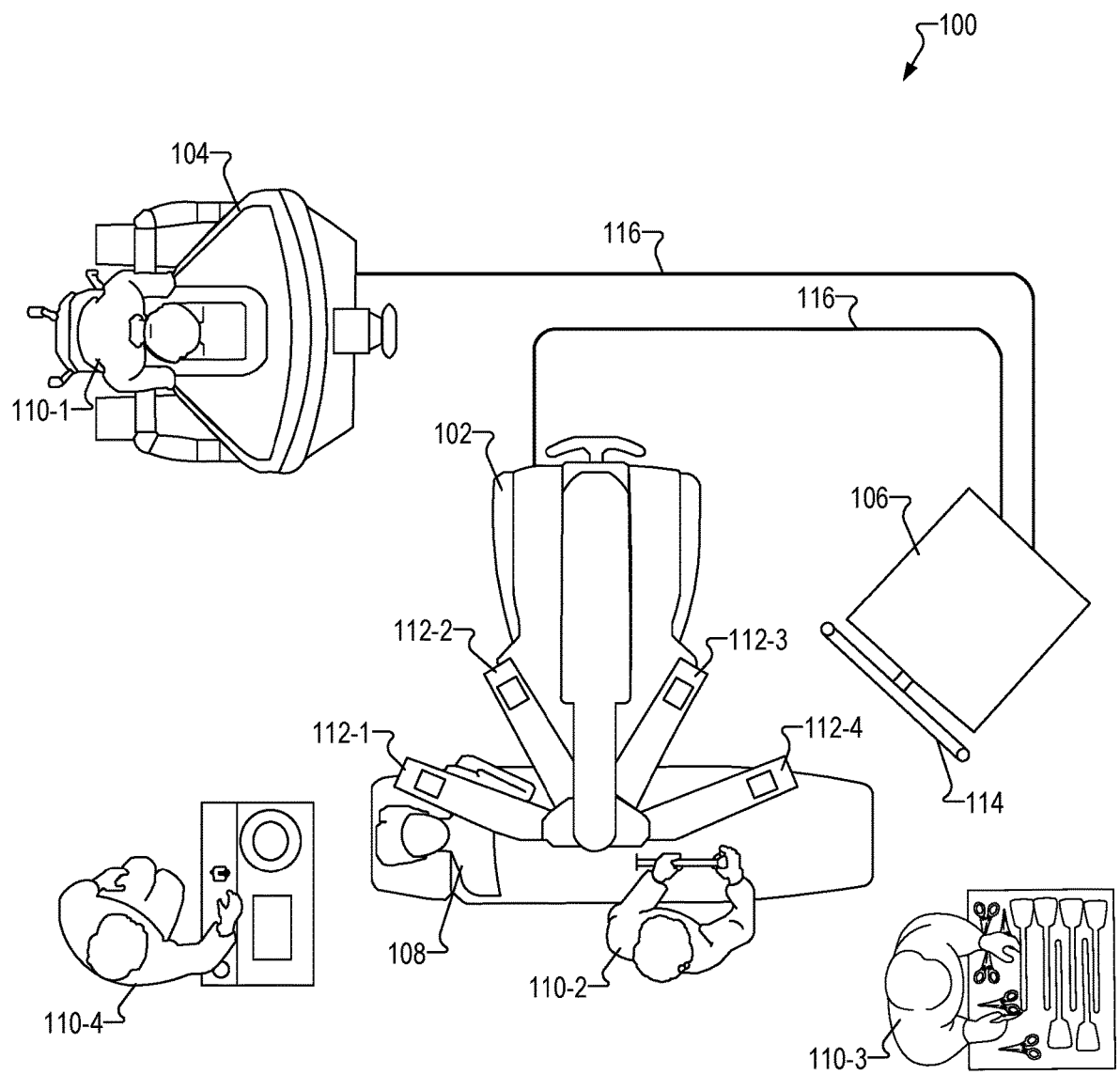
FIG. 1 illustrates an exemplary computer-assisted surgical system according to principles described herein.

Operation profile systems and methods for a computer-assisted surgical system are described herein. As will be explained in more detail below, an exemplary operation profile system may collect surgical session data representative of surgical procedure operations (e.g., operations of a computer-assisted surgical system) performed during a surgical session and may access operation pattern data representative of multiple historical patterns of surgical procedure operations. The operation profile system may identify, based on the operation pattern data and the surgical session data, a first historical pattern included in the multiple historical patterns of surgical procedure operations and that matches a first collected pattern from the surgical procedure operations. The operation profile system may provide, for use (e.g., by the computer-assisted surgical system) during the surgical session, an operation profile associated with the first historical pattern that matches the first collected pattern.

To illustrate, during a minimally-invasive surgical procedure performed with a computer-assisted surgical system, a surgeon may interact with a set of master controls and a set of foot pedals to control teleoperated surgical instruments to perform a surgical procedure. An operation profile system may track the surgeon's interactions with the surgical system during the surgical procedure and may track the surgical system's responses to the surgeon's interactions. For example, the operation profile system may collect data indicating the surgeon's interactions with the master controls and foot pedals, such as data indicating velocity, direction, and shape of the surgeon's movement of master controls and data indicating force and velocity with which the surgeon presses the foot pedals.

Based on the tracked surgeon interactions and surgical system responses, the operation profile system may identify and select, from among a plurality of operation profiles, a distinct operation profile for use by the surgical system during the surgical session. Each operation profile may be based on a unique pattern of operations of a surgical system (e.g., a unique pattern of user interactions and/or surgical system responses to user interactions). In some examples, the operation profile may have been generated based on historical surgical session data indicating similar patterns of interactions by one or more groups of surgeons with one or more computer-assisted surgical systems. Accordingly, the operation profile system may identify a distinct operation profile that is associated with a distinct historical pattern of operations that closely matches the surgeon's interactions with the master controls and foot pedals and the surgical system's responses to the surgeon's interactions.

The operation profile system may then provide the selected operation profile to the computer-assisted surgical system for use by the computer-assisted surgical system during the surgical session. The operation profile may include information that may be used by the surgical system, such as values for various system settings (e.g., ergonomic settings, endoscopic camera settings, image display settings, etc.), warning messages to be presented to the surgeon, and/or instructions for the user. For example, the operation profile may direct the surgical system to adjust the ergonomic positions for the master controls to a certain location that is optimized for users having similar patterns of interactions. Additionally, the operation profile may direct the surgical system to present a warning message to warn the surgeon of events (e.g., manipulator arm collisions) that frequently occur for users having similar patterns of interactions. As another example, if the operation profile is based on interactions by novice users, the operation profile may direct the surgical system to present a message that explains how to perform a particular surgical procedure, or how to perform a particular surgical procedure more efficiently (e.g., use smaller movements, adjust the position or angle of a surgical instrument, etc.).

Various benefits may be provided by the operation profile systems and methods described herein. For example, the systems and methods described herein may passively identify an operation profile of a computer-assisted surgical system based on current operations of the computer-assisted surgical system. In this way, a user of the computer-assisted surgical system (e.g., a surgeon, an assistant, a nurse, etc.) need not actively identify himself or herself to the surgical system, such as by entering user credentials for authentication, but may instead focus on performing the surgical procedure.

Additionally, the systems and methods described herein may collect and use information from other users having similar or superior skillsets and operation profiles to improve a current surgical session. For example, the systems and methods described herein may automatically predict, based on an operation profile associated with a current pattern of operations, certain events that are likely to occur (e.g., instrument collisions), and warn the user of such events. Furthermore, the systems and methods described herein may automatically customize and configure various system settings for the particular user interacting with the computer-assisted surgical system. For example, the systems and methods described herein may automatically adjust ergonomic positions of system components (e.g., master controls, a stereo viewer, an armrest, etc.), automatically adjust endoscopic camera settings (e.g., an exposure level), and automatically adjust image display settings (e.g., a brightness level, a zoom level, a fluorescence imagery display color, etc.).

Various embodiments will now be described in more detail with reference to the figures. The systems and methods described herein may provide one or more of the benefits mentioned above and/or various additional and/or alternative benefits that will be made apparent herein.

The operation profile systems and methods described herein may be implemented as part of or in conjunction with a computer-assisted surgical system. As such, an exemplary computer-assisted surgical system will now be described. The following exemplary computer-assisted surgical system is illustrative and not limiting, as the operation profile systems and methods described herein may be implemented as part of or in conjunction with other suitable surgical systems.

FIG. 1 illustrates an exemplary computer-assisted surgical system 100 ("surgical system 100"). As shown, surgical system 100 may include a manipulating system 102, a user control system 104, and an auxiliary system 106 communicatively coupled one to another. In some examples, surgical system 100 may be implemented by one or more of these components. However, surgical system 100 is not limited to these components, and may include additional components as may suit a particular implementation, such as but not limited to a patient operating table, third-party components (e.g., electrosurgical units) connected to surgical system 100, and the like.

Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation.

While FIG. 1 illustrates an ongoing minimally invasive surgical procedure, surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an intraoperative phase of a surgical procedure, as is illustrated in FIG. 1, but may also include preoperative, postoperative, and/or other suitable phases of the surgical procedure. A surgical procedure may include any procedure in which manual and/or instrumental techniques are used on a patient to investigate, diagnose, or treat a physical condition of the patient. Additionally, a surgical procedure may include any non-clinical procedure, e.g., a procedure that is not performed on a live patient, such as a calibration or testing procedure, a training procedure, and an experimental or research procedure. A preoperative phase may include any actions that are performed prior to the surgical system 102 interacting with the patient, such as setup of surgical system 100, draping manipulating system 102, positioning and/or targeting manipulating system 102, preparing surgical instruments, preparing the operating room, and the like. The intraoperative phase may include any actions that are performed with respect to the patient. The postoperative phase may include any actions that are performed after the intraoperative phase, such as take-down of surgical system 100, cleaning and/or sterilizing surgical system 100, surgical instruments, and/or the operating room, storing surgical system 100 and/or surgical instruments, removing the patient from the operating room, and the like.

As shown in FIG. 1, manipulating system 102 may include a plurality of manipulator arms 112 (e.g., manipulator arm 112-1 through 112-4) to which a plurality of surgical instruments (not shown in FIG. 1) may be coupled. Each surgical instrument may be implemented by any suitable surgical tool (e.g., a tool having tissue-interaction functions), medical tool, monitoring instrument (e.g., an endoscope), sensing instrument (e.g., a force-sensing surgical instrument), diagnostic instrument, or the like that may be used for a computer-assisted surgical procedure (e.g., by being at least partially inserted into patient 108 and manipulated to perform a computer-assisted surgical procedure on patient 108). While manipulating system 102 is depicted and described herein as including four manipulator arms 112, it will be recognized that manipulating system 102 may include only a single manipulator arm 112 or any other number of manipulator arms as may serve a particular implementation.

Manipulator arms 112 and/or surgical instruments attached to manipulator arms 112 may include one or more sensors (e.g., displacement transducers, orientational sensors, positional sensors, etc.) used to generate (i.e., uncorrected) kinematics information (hereinafter "surgical system sensors"). Kinematics information may include information such as pose (e.g., position and/or orientation), movement (e.g., velocity, direction, acceleration, etc.), state (e.g., open, closed, stowed, etc.), and/or other attributes of manipulator arms 112, surgical instruments coupled to manipulator arms 112, and/or any other components of manipulating system 102 (e.g., boom arms). One or more components of surgical system 100 may be configured to use the kinematics information to track (e.g., determine poses, movements, and/or states of) and/or control manipulator arms 112 and/or surgical instruments. Manipulating system 102 may also include other sensors configured to generate other information as may suit a particular implementation. Such sensors may also be referred to as "surgical system sensors" and may include, for example, draping sensors, boom height sensors, and the like.

Surgical instruments attached to manipulator arms 112 may each be positioned at a surgical area associated with a patient. A "surgical area" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located. In other examples, a surgical area may be at least partially disposed external to the patient at or near where a surgical procedure is planned to be performed, is being performed, or has been performed on the patient. For instance, surgical system 100 may be used to perform an open surgical procedure such that part of the surgical area (e.g., tissue being operated on) is internal to the patient while another part of the surgical area (e.g.; a space around the tissue where one or more surgical instruments may be disposed) is external to the patient. A surgical instrument may be referred to as being positioned or located at or within a surgical area when at least a portion of the surgical instrument (e.g., a distal portion of the surgical instrument) is located within the surgical area.

User control system 104 may be configured to facilitate control by surgeon 110-1 of surgical system 100 (e.g., manipulator arms 112 and surgical instruments attached to manipulator arms 112). For example, surgeon 110-1 may interact with user input devices included in user control system 104 to remotely move or manipulate manipulator arms 112 and the surgical instruments coupled to manipulator arms 112. To this end, user control system 104 may provide surgeon 110-1 with imagery (e.g., high-definition stereoscopic imagery) of a surgical area associated with patient 108 as captured by an imaging device (e.g., a stereoscopic endoscope). Surgeon 110-1 may utilize the imagery to perform one or more procedures with one or more surgical instruments coupled to manipulator arms 112.

To facilitate control of surgical instruments, user control system 104 may include a set of master controls (not shown in FIG. 1). These master controls may be manipulated by surgeon 110-1 to control movement of surgical instruments (e.g., by utilizing robotic and/or teleoperation technology). The master controls may be configured to detect a wide variety of hand, wrist, and finger movements by surgeon 110-1. In this manner, surgeon 110-1 may intuitively perform a surgical procedure using one or more surgical instruments.

User control system 104 may further be configured to facilitate control by surgeon 110-1 of other components of surgical system 100. For example, surgeon 110-1 may interact with user control system 104 to change a configuration or operating mode of surgical system 100, to change a display mode of surgical system 100, to generate additional control signals used to control surgical instruments attached to manipulator arms 112, to facilitate switching control from one surgical instrument to another, or to perform any other suitable operation. To this end, user control system 104 may also include one or more additional user input devices (e.g., foot pedals, buttons, switches, touchscreen displays, etc.) configured to receive manual input from surgeon 110-1. In some examples, user control system 104 may also include one or more audio input devices (e.g., microphones) configured to receive audio input (e.g., voice input) from one or more users, and one or more audio output devices (e.g., speakers).

Auxiliary system 106 may include one or more computing devices configured to perform primary processing operations of surgical system 100, The one or more computing devices included in auxiliary system 106 may control and/or coordinate operations performed by various other components (e.g., manipulating system 102 and/or user control system 104) of surgical system 100. For example, a computing device included in user control system 104 may transmit instructions to manipulating system 102 by way of the one or more computing devices included in auxiliary system 106. As another example, auxiliary system 106 may receive, from manipulating system 102 (e.g., from an imaging device), and process image data representative of imagery captured by an endoscope attached to a manipulator arm 112.

In some examples, auxiliary system 106 may be configured to present visual content to surgical team members 110 who may not have access to the imagery provided to surgeon 110-1 at user control system 104. To this end, auxiliary system 106 may include a display monitor 114 configured to display one or more user interfaces, such as images (e.g., 2D images) of the surgical area, information associated with patient 108 and/or the surgical procedure, and/or any other visual content as may serve a particular implementation. For example, display monitor 114 may display images of the surgical area together with additional content (e.g., graphical content, contextual information, etc.) concurrently displayed with the images. In some embodiments, display monitor 114 is implemented by a touchscreen display with which surgical team members 110 may interact (e.g., by way of touch gestures) to provide user input to surgical system 100.

While auxiliary system 106 is shown in FIG. 1 as a separate system from manipulating system 102 and user control system 104, auxiliary system 106 may be included in, or may be distributed across, manipulating system 102 and/or user control system 104. Additionally, while user control system 104 has been described as including one or more user input devices and/or audio input devices, other components of surgical system 100 (e.g., manipulating system 102 and/or auxiliary system 106) may include user input devices, audio input devices, and/or audio output devices as may suit a particular implementation.

Manipulating system 102, user control system 104, and auxiliary system 106 may be communicatively coupled one to another in any suitable manner. For example, as shown in FIG. 1, manipulating system 102, user control system 104, and auxiliary system 106 may be communicatively coupled by way of control lines 116, which may represent any optical, wired, or wireless communication link as may serve a particular implementation. To this end, manipulating system 102, user control system 104, and auxiliary system 106 may each include one or more optical, wired, or wireless communication interfaces, such as one or more local area network interfaces, Wi-Fi network interfaces, cellular interfaces, etc.

Figure 2:
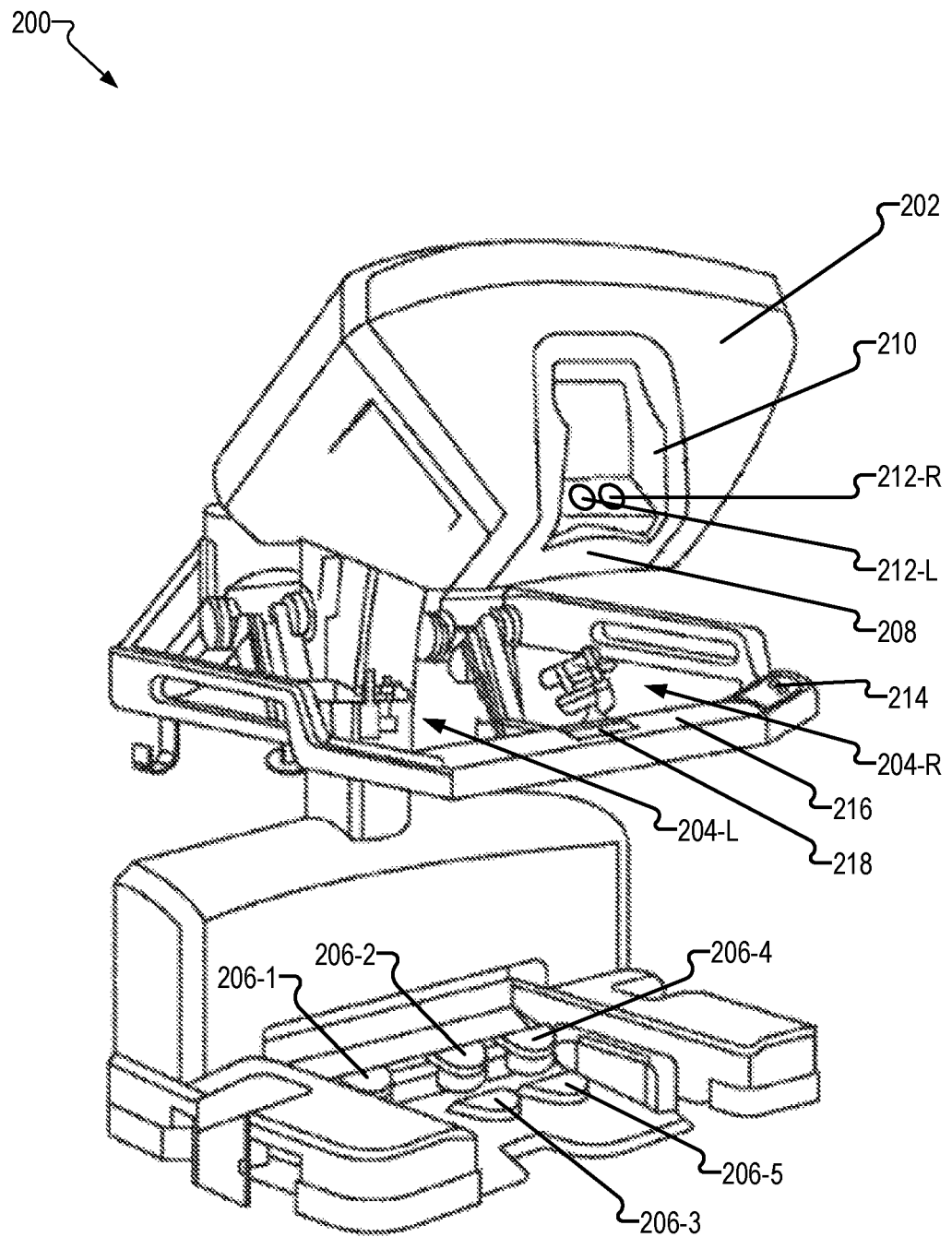
FIG. 2 illustrates an exemplary user control system that may be included within the computer-assisted surgical system of FIG. 1 according to principles described herein.

FIG. 2 illustrates an exemplary user control system 200 with which a user (e.g.; surgeon 110-1) may interact to control various operations of a computer-assisted surgical system (e.g., surgical system 100). In some examples, user control system 200 implements user control system 104.

As shown, user control system 200 includes a display module 202, a set of master controls 204 (e.g., a left master control 204-L and a right master control 204-R), and a set of foot pedals 206 (e.g., foot pedals 206-1 through 206-5). User control system 200 may include additional or alternative components as may serve a particular implementation. For example, user control system 200 may include various computing components (e.g., processors, memory, etc.), support structures (e.g., a base, a column, etc.), adjustment mechanisms (e.g., pivots, motors, etc.), user input devices, and the like.

Display module 202 includes an image display system 208, a viewer console 210, and eyepieces 212 (e.g., a left eyepiece 212-L and a right eyepiece 212-R). Image display system 208 is configured to present imagery generated by surgical system 100, such as imagery of a surgical area associated with a patient as captured by a stereoscopic endoscope. Imagery presented by image display system 208 may be viewed through eyepieces 212 when the user's head is positioned in viewer console 210.

In some examples, display module 202 (e.g., viewer console 210) may also include one or more head sensors (not shown in FIG. 2) configured to detect a presence of a head of a user within a vicinity of viewer console 210. Display module 202 (e.g., image display system 208) may also include one or more eye sensors (not shown in FIG. 2) configured to detect a presence of an eye of a user when the user is viewing imagery through eyepieces 212. The head sensor(s) and/or eye sensor(s) may be used by surgical system 100 to determine a user's presence at user control system 200 and/or intent to interact with user control system 200.

Figure 3:
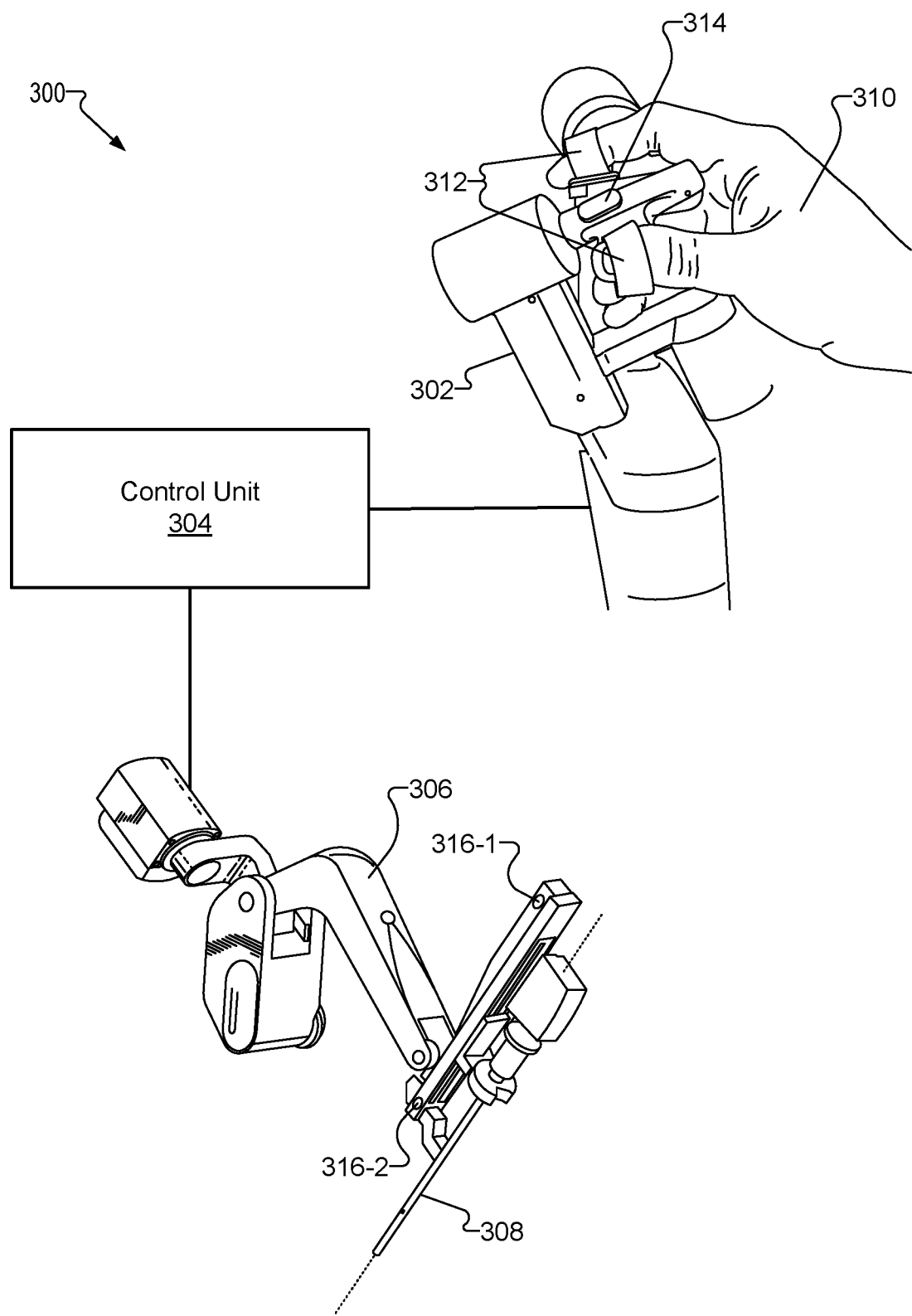
FIG. 3 illustrates an exemplary master control system that may be included within the computer-assisted surgical system of FIG. 1 according to principles described herein.

Master controls 204 (e.g., master control 204-L and master control 204-R) may be manipulated by a surgeon to control movement of surgical instruments (e.g., by utilizing robotic and/or teleoperation technology). FIG. 3 illustrates an exemplary master control system 300 including a master control 302 that may be used in accordance with the systems and methods described herein to facilitate control of various operations of a computer-assisted surgical system (e.g., surgical system 100). In some examples, master control 302 implements master control 204-R.

As shown in FIG. 3, master control system 300 includes master control 302 and a control unit 304. Master control 302 is communicatively coupled to control unit 304, and control unit 304 is communicatively coupled to a manipulator arm 306 and/or a surgical instrument 308 (e.g., by way of manipulator arm) coupled to manipulator arm 306. Manipulator arm 306 may be a manipulator arm of surgical system 100, such as any of manipulator arms 112-1 through 112-4. Surgical instrument 308 may be any suitable surgical instrument and may be physically coupled to manipulator arm 306 in any suitable way. As will be explained below in more detail, control unit 304 is configured to translate movements of master control 302 into corresponding movements of manipulator arm 306 and/or surgical instrument 308.

As shown in FIG. 3, master control 302 is configured to be manipulated by a right hand 310 of a surgeon (e.g., surgeon 110-1). A left hand master control (not shown in FIG. 3) may be similar to master control 302, and therefore discussion of the left hand master control is omitted. Master control 302 may include a variety of mechanisms (e.g., buttons, finger loops, levers, pivot points, etc.) configured to receive a wide variety of hand, wrist, and finger movements by a surgeon to control movement of surgical instruments. For example, as shown in FIG. 3, master control 302 includes finger loops 312 configured to receive a finger and/or a thumb of the surgeon. Accordingly, the surgeon may manipulate master control 302 in various ways and with multiple degrees of freedom in order to telemanipulate surgical instrument 308.

In some examples, master control 302 may also include a user input device 314 by which the surgeon may provide input, such as to indicate a particular mode of operation (e.g., a clutch mode of operation). User input device 314 may be implemented as any suitable type of input mechanism, such as a button, a switch, a toggle input, a directional pad, a joystick, etc. User input device 314 may be positioned on master control 302 at any suitable location.

Control unit 304 may be communicatively coupled to master control 302, manipulator arm 306, and surgical instrument 308 in any suitable way that allows data, communications, and/or other signals to be sent and/or received by control unit 304 to/from master control 302, manipulator arm 306, and/or surgical instrument 308. In some examples, control unit 304 may be implemented within one or more components of surgical system 100, such as within manipulating system 102, user control system 104, and/or auxiliary system 106. Control unit 304 may be implemented as hardware and/or software configured to control various operations of the computer-assisted surgical system, including manipulator arm 306 and/or surgical instrument 308.

Control unit 304 may be configured to receive information from master control 302. For example, control unit 304 may receive information regarding a pose, movement (e.g., velocity, direction, acceleration, etc.), state, etc. of master control 302 and/or information regarding user interaction with master control 302 (e.g., hand presence, a force of a user's grip of master control 302, etc.). Based on such information, control unit 304 may track the pose, movement, state, and/or other attributes of master control 302.

When operating in certain operating modes (e.g., a normal mode of operation), control unit 304 may process the information received from master control 302 to generate information and/or signals to send to manipulator arm 306 to cause manipulator arm 306 and/or surgical instrument 308 to operate in accordance with the information received from master control 302. In this or a similar manner, control unit 304 may translate attributes of master control 302 into corresponding operations of manipulator arm 306 and/or surgical instrument 308, such as by translating movement of master control 302 into corresponding movement of manipulator arm 306 and/or surgical instrument 308. In this way, control unit 304 couples master control 302 to manipulator arm 306 and/or surgical instrument 308 such that a surgeon may telemanipulate surgical instrument 308 attached to manipulator arm 306 using master control 302.

When operating in certain other operating modes, control unit 304 may output different information to manipulator arm 306 and/or may output information to other components of the computer-assisted surgical system (e.g., to image display system 208). When operating in some operating modes, control unit 304 may output no information to manipulator arm 306 or surgical instrument 308, such as when operating in a clutch mode of operation in which master control system 300 decouples master control 302 from controlling movement of manipulator arm 306 and/or surgical instrument 308.

Manipulator arm 306 and/or surgical instrument 308 may also be configured to be manually moved by a user to adjust a pose of manipulator arm 306 and/or surgical instrument 308. In some embodiments, manipulator arm 306 and/or surgical instrument 308 may include one or more user input devices 316 (e.g., user input device 316-1 and user input device 316-2) configured, upon activation by the user, to enable manual movement by the user. For example, user input devices 316 may decouple manipulator arm 306 and/or surgical instrument 308 from control unit 304 and/or otherwise unlock manipulator arm 306 and/or surgical instrument 308 to enable manual adjustment.

Referring again to FIG. 2, foot pedals 206 (e.g., foot pedals 206-1 through 206-5) facilitate control of various components of the computer-assisted surgical system 100 (e.g., surgical instruments coupled to manipulator arms 112). For example, foot pedals 206 may enable surgeon 110-1 to perform various operations, such as swapping control of surgical instruments, controlling features of an imaging system (e.g., an endoscope), and activating surgical instrument features (e.g., energizing a cautery instrument, firing a stapling instrument, etc.). While FIG. 2 shows five foot pedals 206, user control system 200 may have fewer or more foot pedals as may suit a particular implementation.

In some examples, user control system 200 may also include one or more auxiliary user input devices to allow a user to control various components or settings of user control system 200 and/or the computer-assisted surgical system other than surgical instruments and/or manipulator arms. For example, as shown in FIG. 2, user control system 200 includes a set of user input devices 214 (e.g., soft buttons, hard buttons, knobs, dials, joysticks, etc.) that may be manually operated by the user to effectuate a positional adjustment of one or more components of user control system 200. To illustrate, user control system 200 may be configured to adjust a position (e.g., height, extension, tilt, etc.) of one or more components of display module 202 (e.g., master controls 204, foot pedals 206, eyepieces 212, an armrest 216, etc.) to optimize ergonomics for the user. As shown in FIG. 2, user input devices 214 are located on armrest 216. However, user input devices 214 are not limited to this location, and may be located on user control system 200 at any other suitable location(s).

Additionally, as shown in FIG. 2, user control system 200 may include a touchscreen display 218 with which a user of user control system 200 may view content and interact (e.g., by way of touch gestures) to provide user input to the computer-assisted surgical system. Touchscreen display 218 may present content such as user login information, surgical team member information, system settings information (e.g., user control system settings, ergonomic position settings, imaging mode settings, etc.) and/or any other visual content (e.g., notifications, messages, etc.) as may serve a particular implementation. Additionally or alternatively, touchscreen display 218 may include an operation panel (e.g., a number pad, a keypad, a set of soft and/or hard buttons, etc.) configured to receive user input (e.g., a username, a password, user profile information, user preference information, system settings information, etc.). As shown in FIG. 2, touchscreen display 218 is positioned at a center portion of armrest 216. However, touchscreen display 218 may be positioned on user control system 200 at any other location as may suit a particular implementation.

As described above, a computer-assisted surgical system (e.g., surgical system 100) may include various user input devices and components with which users may interact. In some examples, the various user input devices and system components may include one or more sensors configured to measure and detect various interactions by a user, such as when the user input devices are actuated or manipulated, when surgical instruments are coupled to/removed from a manipulator arm, when surgical instruments are inserted into/removed from a patient, when a functional feature of a surgical instrument is operated (e.g., energy is applied, end effectors are opened or closed, stapling instrument is fired, etc.), when a foot pedal is pressed, a duration of actuation or manipulation of a user input device, a force with which a user interacts with a user input device or system component (e.g., presses a button, moves a manipulator arm 112, etc.), and the like. Any suitable sensors may be used, such as but not limited to proximity sensors, force sensors, piezoelectric sensors, image sensors, displacement transducers, orientational sensors, positional sensors, accelerometers, gyroscopes, magnetometers, and the like. These sensors may also be referred to herein as "surgical system sensors."

Interactions, by one or more users, with the computer-assisted surgical system, and the computer-assisted surgical system's responses to such user interactions, may exhibit unique patterns and tendencies. As described herein, an operation profile system may be configured to identify and exploit these unique patterns and tendencies to improve operations of the computer-assisted surgical system during a surgical session.

Figure 4:
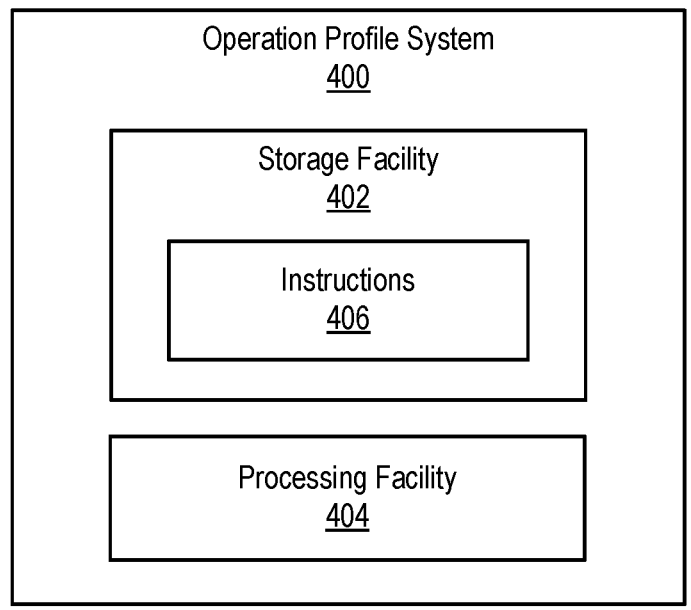
FIG. 4 illustrates an exemplary operation profile system according to principles described herein.

FIG. 4 illustrates an exemplary operation profile system 400 ('system 400") configured to identify, based on tracked surgical procedure operations (e.g., operations of a computer-assisted surgical system and/or operations performed manually by a user), an operation profile and provide the operation profile for use during a surgical session. As shown, system 400 may include, without limitation, a storage facility 402 and a processing facility 404 selectively and communicatively coupled to one another. Facilities 402 and 404 may each include or be implemented by hardware and/or software components (e.g., processors, memories, communication interfaces, instructions stored in memory for execution by the processors, etc.). In some examples, facilities 402 and 404 may be distributed between multiple devices and/or multiple locations as may serve a particular implementation.

Storage facility 402 may maintain (e.g., store, alter, update, etc.) executable data used by processing facility 404 to perform any of the operations described herein. For example, storage facility 402 may store instructions 406 that may be executed by processing facility 404 to perform any of the operations described herein. Instructions 406 may be implemented by any suitable application, software, code, and/or other executable data instance.

Storage facility 402 may also maintain any data received, generated, managed, used, and/or transmitted by processing facility 404. For example, as will be described below in more detail, storage facility 402 may maintain surgical session data, interaction event data, response event data, operation pattern data, operation profile data, user profile data, and the like.

Processing facility 404 may be configured to perform (e.g., execute instructions 406 stored in storage facility 402 to perform) various processing operations associated with automatically identifying an operation profile. For example, processing facility 404 may collect surgical session data representative of surgical procedure operations performed during a surgical session. Processing facility 404 may also access operation pattern data representative of multiple historical patterns of surgical procedure operations. Processing facility 404 may identify, based on the operation pattern data and the surgical session data, a first historical pattern included in the multiple historical patterns of surgical procedure operations and that matches a first collected pattern from the surgical procedure operations. Processing facility 404 may provide, for use (e.g., by the computer-assisted surgical system) during the surgical session, an operation profile associated with the first historical pattern that matches the first collected pattern. These and other operations that may be performed by processing facility 404 are described herein.

In some examples, system 400 is implemented entirely by the computer-assisted surgical system itself. For example, system 400 may be implemented by one or more computing devices included in surgical system 100 (e.g., in one or more computing devices included within manipulating system 102, user control system 104, and/or auxiliary system 106).

Figure 5:
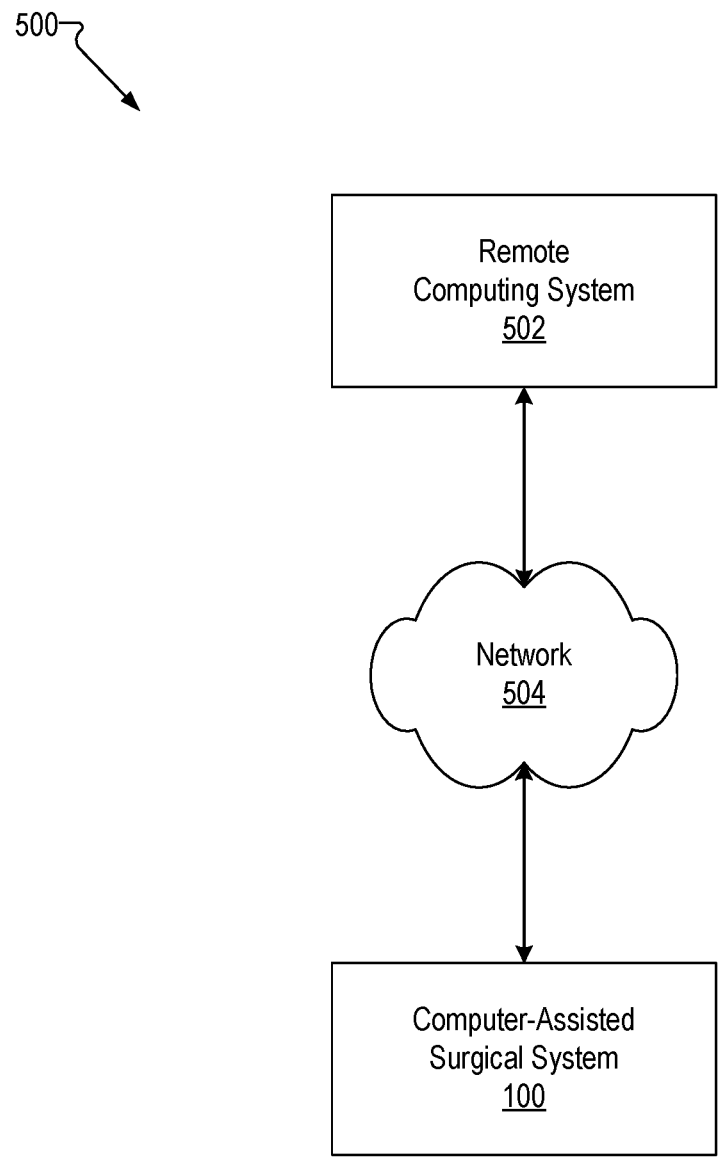
FIG. 5 illustrates an exemplary implementation of the operation profile system of FIG. 4 according to principles described herein.

FIG. 5 illustrates another exemplary implementation 500 of system 400. In implementation 500, a remote computing system 502 may be communicatively coupled to surgical system 100 by way of a network 504, Remote computing system 502 may include one or more computing devices (e.g., servers) configured to perform any of the operations described herein. In some examples, system 400 may be entirely implemented by remote computing system 502. Alternatively, system 400 may be implemented by both remote computing system 502 and surgical system 100.

Network 504 may be a local area network, a wireless network (e.g., Wi-Fi), a wide area network, the Internet, a cellular data network, and/or any other suitable network. Data may flow between components connected to network 504 using any communication technologies, devices, media, and protocols as may serve a particular implementation.

Various operations that may be performed by system 400 (e.g., by processing facility 404 of system 400), and examples of these operations, will now be described. It will be recognized that the operations and examples described herein are merely illustrative of the many different types of operations that may be performed by system 400.

System 400 may be configured to track surgical procedure operations, including operations of a computer-assisted surgical system (e.g., surgical system 100) and/or manual operations performed over time during one or more surgical sessions. Operations of a computer-assisted surgical system may include user interaction events ("interaction events") and/or computer-assisted surgical system response events ("response events"), as will now be described in detail.

Interaction events include distinct interactions, by one or more users (e.g., a surgeon, an assistant, etc.), with the computer-assisted surgical system. Interaction events may include direct user interactions and/or indirect user interactions with the computer-assisted surgical system. A direct user interaction may include any physical interaction, by a user, with a user input device included in the computer-assisted surgical system. Examples of direct user interactions with a user input device may include, without limitation, manipulation of master controls 204, actuation of a system button (e.g., user input device 214, user input device 314, a user input device 316, etc.), actuation of a foot pedal 206, touch input on a touchscreen display (e.g., display monitor 114, touchscreen display 218, etc.), and the like. Additionally or alternatively, a direct user interaction may include any physical interaction, by a user, with a component of the surgical system, such as to adjust a pose and a state of the component. Examples of direct user interactions with a component of the surgical system may include, without limitation, positioning or targeting manipulating system 102 at a patient operating table, manually moving a manipulator arm 112, docking a cannula to a manipulator arm 112, coupling and/or removing a surgical instrument from a manipulator arm 112, inserting a surgical instrument within a patient and/or removing a surgical instrument from the patient, manually re-positioning master controls 204, and the like.

An indirect user interaction may include any non-physical interaction, by a user, with the computer-assisted surgical system. Examples of indirect interactions may include, for example, user interactions based on audio (e.g., voice inputs and/or commands provided to the computer-assisted surgical system), non-physical interactions with surgical system sensors (e.g., moving the user's eyes into a detectable range of an eye sensor included in image display system 208, moving the user's eyes while in a detectable range of the eye sensor, moving the user's head into a detectable range of a head sensor included in viewer console 210, moving the user's head while in a detectable range of the head sensor, hovering the user's foot over a foot pedal 206), and the like. In some examples, an indirect interaction event may also include the absence of interaction, by a user, with the computer-assisted surgical system for a period of time (e.g., for at least three minutes).

As used herein, response events include distinct operations performed by the computer-assisted surgical system in response to interaction events. Response events may include any mechanical, electrical, optical, hardware, and/or software-based operations as may serve a particular implementation. For example, response events may include adjustment of a pose of a component of the surgical system (e.g., moving surgical instrument 308 in response to a corresponding operation of master control 302, adjusting an ergonomic position of master controls 204 and armrest 216, etc.), operation of a functional feature of a surgical instrument (e.g., energizing a cautery instrument, opening and closing forceps or scissors, firing a stapling instrument, etc.), adjustment of a surgical system setting (e.g., adjusting an exposure level or a zoom level of an imaging system, etc.), detection of a system fault or error (e.g., detection of a collision of manipulator arms 112, a collision of surgical instruments, etc.), generation of a fault code, and the like.

As mentioned above, system 400 may track operations of the computer-assisted surgical system. The tracking may include collecting surgical session data representative of operations of the computer-assisted surgical system during one or more surgical sessions. Surgical session data representative of operations of a computer-assisted surgical system may include interaction event data representative of an interaction event and/or response event data representative of a response event.

Interaction event data may indicate one or more attributes of interaction events, such as a force, a pose, a velocity, an acceleration, a state, a trajectory, and/or a timing of the interaction events. To illustrate, interaction event data may indicate a force or acceleration with which a user actuates a user input device (e.g., user input device 314, a user input device 316, etc.), presses a foot pedal 206, touches touchscreen display 218, grips master controls 204, manually moves or adjusts a manipulator arm 112, and the like. A pose of an interaction event may indicate, for example, a position and/or orientation of a user input device (e.g., master controls 204), a half-press of a foot pedal 206, and the like. A state of an interaction event may indicate, for example, an open/closed state of master controls 204, an idle state of a system component, and the like. As another example, interaction event data may indicate a velocity or acceleration with which a user moves master controls 204, manually moves or adjusts a manipulator arm 112, couples or removes a surgical instrument from a manipulator arm 112, moves the user's head within viewer console 210, and the like. As a further example, interaction event data may indicate a trajectory (e.g., in a 3D coordinate system) in which a user moves master controls 204 or manually moves a manipulator arm 112. A timing of an interaction event may indicate a timestamp at which an interaction event occurs (e.g., begins and/or terminates), a duration of an interaction event (e.g., a duration of a user actuation of a button, a duration of manual movement of a manipulator arm 112, and the like), a frequency at which a particular interaction event occurs (e.g., every 3 minutes), a total number of occurrences of a particular interaction event, and the like. These examples of attributes of interaction events are illustrative. Additional or alternative attributes of interaction events may be tracked in other examples.

Response event data may indicate one or more attributes of response events, such as a velocity, an acceleration, a pose, a trajectory, a state, and/or a timing of the response events. To illustrate, response event data may indicate a velocity or acceleration of movement of a surgical instrument. As another example, response event data may indicate a trajectory of movement of a surgical instrument and/or starting and ending poses of the surgical instrument. As a further example, response event data may indicate an opened or closed state of a surgical instrument, an error or fault state of a system component, an energization state of a surgical instrument, a draping completion state, and the like. As another example, a timing of a response event may indicate a timestamp at which a response event occurs, a duration of a response event (e.g., a duration of a fluorescence image display mode, a duration of a particular camera zoom level, etc.), a frequency at which a particular response event occurs (e.g., a frequency of firing staples), a total number of occurrences of a particular response event (e.g., a total number of collisions of manipulator arms 112), and the like. These examples of attributes of response events are illustrative. Additional or alternative attributes of response events may be tracked in other examples.

The surgical session data may be generated by the computer-assisted surgical system (e.g., by manipulating system 102, user control system 104, auxiliary system 106, master control system 300, etc.), by one or more components coupled to the computer-assisted surgical system during the surgical session, and/or by any other device associated with the computer-assisted surgical system as may serve a particular implementation. In scenarios in which system 400 is implemented entirely by remote computing system 502, surgical session data may be generated by surgical system 100 and transmitted to remote computing system 502 via network 504. Thus, remote computing system 502 may track operations of surgical system 100.

Surgical session data (e.g., interaction event data and response event data) generated during a surgical session may include various types of data associated with interaction events and response events. For example, surgical session data generated during a surgical session may include kinematic data, image data, sensor data, surgical instrument data, and/or any other type of data as may serve a particular implementation.

Kinematic data may be representative of a pose of a component within the computer-assisted surgical system and/or a component coupled to the computer-assisted surgical system. For example, kinematic data may be representative of a pose of a manipulator arm 112, a surgical instrument coupled to a manipulator arm 112, master controls 204, and/or any other component of the computer-assisted surgical system as may suit a particular implementation.

Image data may be representative of one or more images captured by an imaging device (e.g., an imaging device coupled to the computer-assisted surgical system). For example, image data may be representative of one or more images captured by an imaging device (e.g., a stereoscopic endoscope) coupled to a manipulator arm 112. The one or more images may constitute one or more still images and/or video captured by the imaging device. In some examples, system 400 may access image data by receiving (e.g., by way of a network) images output by the imaging device. In additional or alternative examples, image data may include image data generated by an imaging device that is external to a patient.

Sensor data may include any data generated by surgical system sensors included in or associated with a computer-assisted surgical system. Sensor data may be representative of any sensed parameter as may serve a particular implementation. In some examples, sensor data may be representative of one or more attributes of interaction events and response events, such as force, velocity, acceleration, trajectory, and timing of the interaction events and response events. In some examples, certain kinematic data and image data may be generated by and/or based on parameters sensed by surgical system sensors. Accordingly, sensor data may include such kinematic data and image data.

Surgical instrument data may include any data generated by a surgical instrument, and may be representative of an identification ("ID") of the surgical instrument, an operational state of the surgical instrument (e.g., open, closed, electrically charged, idle, etc.), a fault code of the surgical instrument, etc.

In some examples, surgical session data may also include data representative of information associated with a particular surgical session. For example, the surgical session data may include data indicating a target anatomy for a particular surgical procedure (e.g., liver, colon, lungs, etc.), a type of surgical procedure (e.g., hernia repair, hysterectomy, biopsy, etc.), a time and date of a particular surgical procedure, surgical team member information for a particular surgical procedure (e.g., user authentication information, a user profile, surgical team member changes, etc.), and the like.

System 400 may collect the surgical session data in any way that is suitable for generation of operation pattern data based on the surgical session data. For example, in implementation 500, surgical system 100 may be configured to provide, over time during a surgical session, surgical session data representative of one or more operations of surgical system 100 to remote computing system 502. As another example, system 400 may store surgical session data in storage facility 402 as the surgical session data is generated.

As mentioned, system 400 may be configured to track surgical procedure operations by collecting surgical session data. In some embodiments, the tracking may also include processing the collected surgical session data to identify one or more patterns of operations and generate, from the surgical session data, operation pattern data representative of the one or more identified patterns of operations. In certain embodiments, system 400 may also be configured to generate one or more operation profiles for the operation pattern data. System 400 may identify patterns of operations, generate operation pattern data, and generate one or more operation profiles in any suitable manner.

Figure 6:
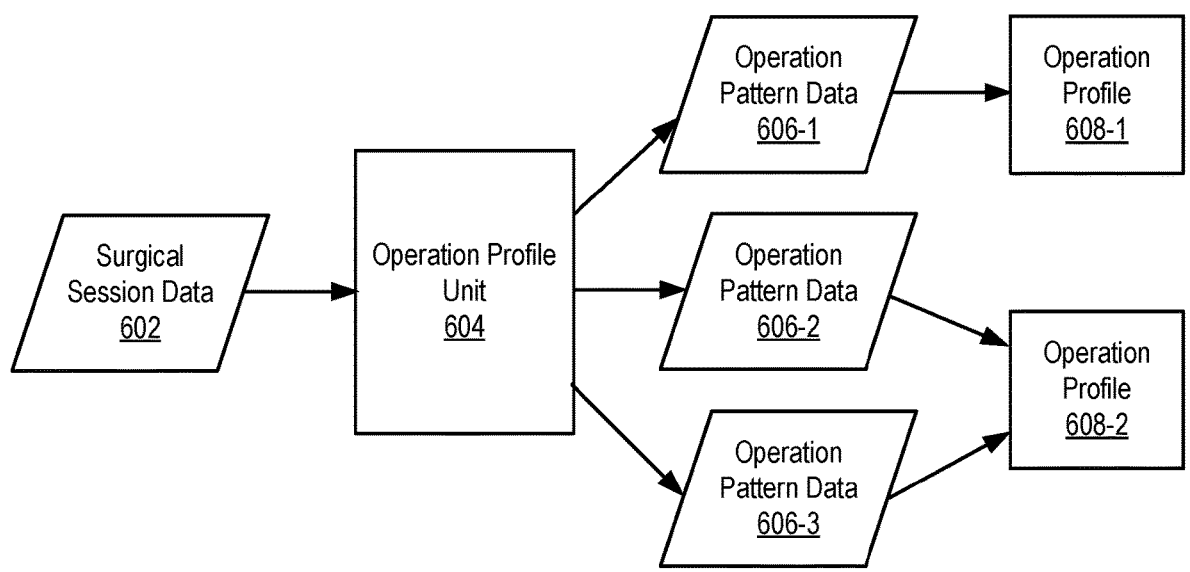
FIG. 6 illustrates an exemplary identification of a plurality of distinct sets of operation pattern data based on surgical session data according to principles described herein.

FIG. 6 illustrates an exemplary manner in which system 400 may process surgical session data to identify, from the collected surgical session data, one or more patterns of operations and generate one or more operation profiles for the identified patterns of operations. As shown, system 400 may apply surgical session data 602 to an operation profile unit 604. Operation profile unit 604 may perform any suitable heuristic, process, and/or operation that may be performed or executed by system 400 and that may be configured to identify one or more patterns of operations and generate one or more distinct sets of operation pattern data. In some examples, operation profile unit 604 may be implemented by hardware and/or software components (e.g., processors, memories, communication interfaces, instructions stored in memory for execution by the processors, etc.), such as storage facility 402 and/or processing facility 404 of system 400.

Operation profile unit 604 may analyze surgical session data 602 and identify one or more distinct patterns of operations from the surgical session data 602 in any suitable way. In some examples, a distinct pattern of operations may be identified based on an attribute, or a combination of attributes, of operations of a computer-assisted surgical system, as represented by interaction event data and/or response event data. As an example, certain surgical session data may indicate a pattern of activating user input devices (e.g., buttons, foot pedals, etc.) with a particular amount of force. Additionally or alternatively, certain surgical session data may indicate a pattern of activating a particular image display mode (e.g., a fluorescence display mode) for a particular duration of time and at certain timing during a surgical session. As another example, video data may indicate a certain pattern with which a user manually performs a surgical procedure operation. Operation profile unit 604 may detect these operation patterns and use the surgical session data for each operation pattern to generate a distinct set of operation pattern data for each distinct operation pattern.

For example, FIG. 6 shows operation profile unit 604 generating and outputting a first set of operation pattern data 606-1, a second set of operation pattern data 606-2, and a third set of operation pattern data 606-3. Operation pattern data 606-1 may contain operation pattern data representative of a first distinct historical pattern of operations, operation pattern data 606-2 may contain data representative of a second distinct historical pattern of operations, and operation pattern data 606-3 may contain data representative of a third distinct historical pattern of operations. In some examples, multiple distinct operation patterns may be based on a common subset of interaction events and/or response events. For instance, operation pattern data 606-1 may indicate a unique pattern of pressing foot pedals 206, and operation pattern data 606-2 may indicate the same pattern of pressing foot pedals 206 in combination with a unique pattern of pressing buttons (e.g., user input devices 314 and 316).

Each set of operation pattern data may be stored to, or associated with, one or more distinct operation profiles 608. For example, as shown in FIG. 6, operation pattern data 606-1 may be stored to a first operation profile 608-1, operation pattern data 606-2 may be stored to a second operation profile 608-2, and operation pattern data 606-3 may also be stored to second operation profile 608-2. Accordingly, each of the distinct operation profiles 608-1 and 608-2 may include a distinct set of operation pattern data 606 representative of a distinct operation pattern. For instance, operation pattern data 606-1 included in operation profile 608-1 may represent a distinct operation pattern in which master controls 204 are operated with a particular velocity and trajectory of motion, operation pattern data 606-2 included in operation profile 608-2 may represent a distinct operation pattern in which master controls 204 are operated with a different, distinct pattern of velocity and trajectory of motion, and operation pattern data 606-3 included in operation profile 608-2 may represent a distinct operation pattern in which energization of electrosurgical instruments is frequently excessive.

Operation pattern data 606 may be in any format. In some examples, operation pattern data 606 is stored in the same format in which surgical session data 602 is received by operation profile unit 604. In additional or alternative examples, operation pattern data 606 is stored as a bit-encoded value and/or a hash/digest. For instance, operation profile unit 604 may apply the surgical session data 602 representative of each distinct pattern of operations as inputs to a hash function and output, as each distinct set of operation pattern data 606, a distinct hash or digest. Operation profile unit 604 may apply any suitable hash function as may suit a particular implementation.

In some embodiments, system 400 does not track which user of a group of users is interacting with the computer-assisted surgical system. Instead, system 400 may detect and assign operation pattern data representative of the distinct patterns of operations to separate operation profiles, as described above.

In alternative embodiments, the computer-assisted surgical system may track which user of a group of users is interacting with the computer-assisted surgical system. For example, the computer-assisted surgical system may prompt each user to login in order to interact with the computer-assisted surgical system. In such embodiments, surgical session data and/or operation pattern data provided while a user is logged in may be associated with and/or stored to a user profile of the user. Additionally or alternatively, an operation profile associated with the identified operation pattern data may be stored to and/or associated with the user profile.

In some examples, an operation profile may be associated one-to-one with a particular user and/or with a particular user profile for the user. For instance, operation profile 608-1 may include operation pattern data that represents patterns of operations based on interactions by only a first user (e.g., surgeon 110-1), and operation profile 608-2 may include operation pattern data that represents patterns of operations based on interactions by only a second user (e.g.; assistant 110-2).

In other examples, operation profiles 608 may not coincide one-to-one with users of the computer-assisted surgical system or the user profiles for the users. In these examples, a user profile may be associated with multiple operation profiles each representing a distinct pattern of operations exhibited by the user. For instance, operation profile 608-1 may include operation pattern data that represents a first pattern of operations (e.g., based on how the user typically interacts with the computer-assisted surgical system for a first type of surgical procedure, such as a hernia repair surgery), and operation profile 608-2 may include operation pattern data that represents a second pattern of operations by the same user (e.g., based on how the user typically interacts with the computer-assisted surgical system for a second type of surgical procedure, such as a hysterectomy).

The above-described examples of operation pattern data have been described with reference to operations of a single computer-assisted surgical system. Such operation pattern data may be referred to as "local operation pattern data," which may include any operation pattern data that is generated exclusively from surgical session data provided by a single computer-assisted surgical system.

Additionally or alternatively, operation pattern data generated and maintained by system 400 may be generated from global surgical session data, e.g., surgical session data provided by one or more other computer-assisted surgical systems or by a combination of surgical system 100 and one or more other surgical systems. This type of operation pattern data may be referred to as "global operation pattern data," which may include any operation pattern data that is generated from an aggregation of surgical session data provided by multiple computer-assisted surgical systems (e.g., one or more surgical systems other than surgical system 100, or a combination of surgical system 100 and one or more other surgical systems).

Global operation pattern data may represent one or more patterns of operations based on an aggregation of interactions by one or more users and/or with one or more computer-assisted surgical systems. Thus, global operation pattern data may represent any of the operation patterns described herein in relation to local operation pattern data, except that the operation patterns represented by the global operation pattern data represent global operation patterns in the aggregate across multiple computer-assisted surgical systems, users, and/or surgical sessions. The global surgical session data may be generated based on interactions with a particular group of computer-assisted surgical systems (e.g., within a particular hospital network), by a particular group of users (within a particular hospital), and/or during a particular group of surgical procedures (e.g., hernia repair procedures).

The above-described examples describe identifying one or more distinct patterns of operations and generating operation pattern data based on surgical session data collected during a surgical session. However, in other examples operation patterns may be defined, and operation pattern data may be generated, without using a specific set of surgical session data collected during a surgical session. In these examples an operation pattern may be constructed without surgical session data, such as by using an operation pattern rule or a specification language. For instance, a user may manually prescribe values of attributes represented by interaction event data and/or response event data for a theoretical operation pattern. In additional or alternative examples, operation pattern data generated based on collected surgical session data may be manually adjusted or corrected, such as to correct anomalies or account for external factors not sensed or accounted for by the surgical system.

As mentioned, system 400 may be configured to track surgical procedure operations by collecting surgical session data generated during a current surgical session. In some embodiments, system 400 may be configured to use the surgical session data collected during the current surgical session to select and provide a previously-generated operation profile (e.g., an operation profile generated based on historical surgical session data) for use during the current surgical session. For example, system 400 may identify a first historical pattern that matches the current surgical session data (e.g., a pattern from the currently-collected surgical session data). System 400 may then select and provide, for use (e.g., by the computer-assisted surgical system) during the current surgical session, an operation profile associated with the first historical pattern. Examples of selecting and providing the operation profile to the computer-assisted surgical system will now be described.

Figure 7:
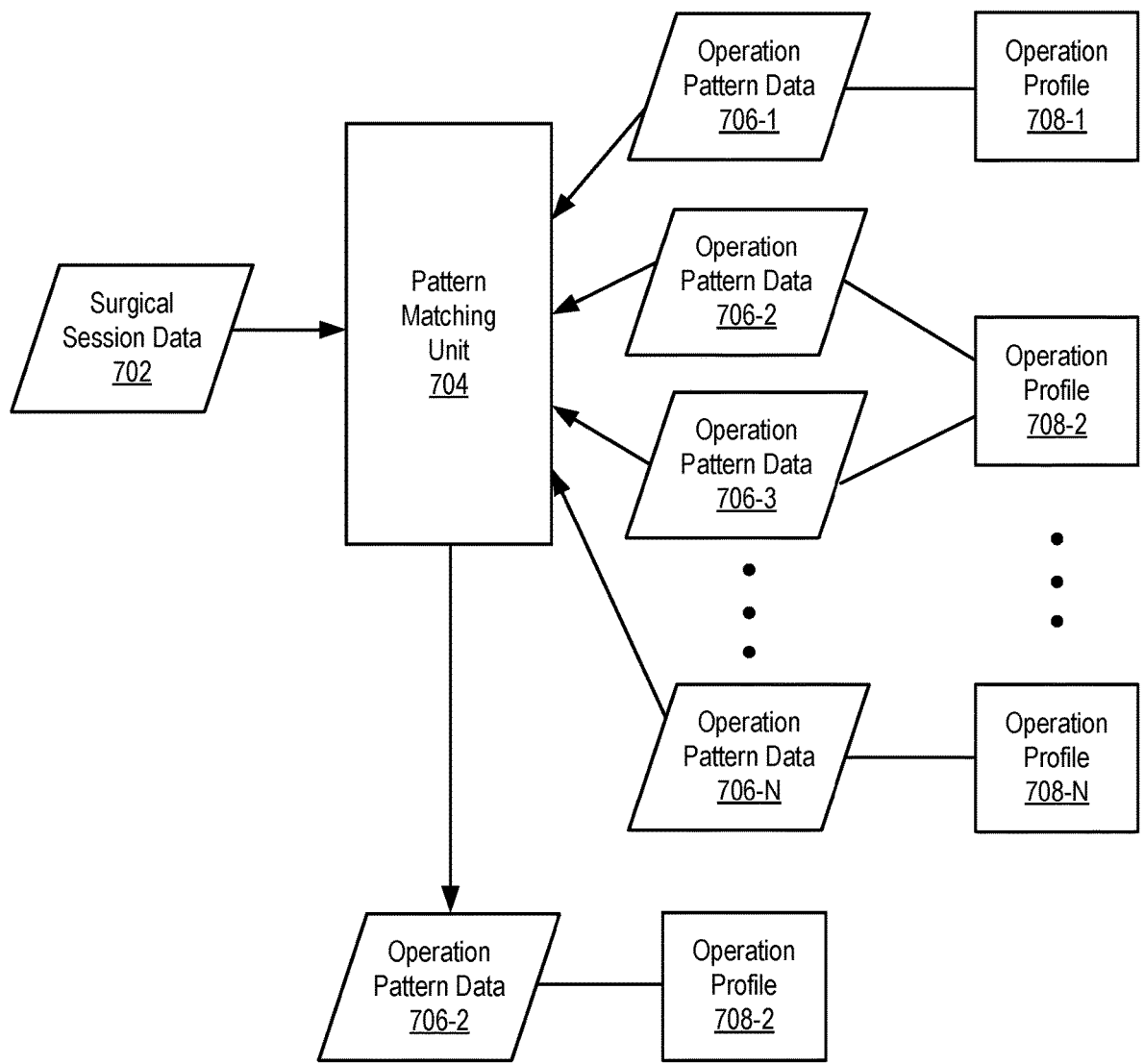
FIG. 7 illustrates an exemplary identification of a distinct set of operation pattern data based on surgical session data and selection of an operation profile according to principles described herein.

FIG. 7 illustrates an exemplary manner in which system 400 may select an operation profile based on surgical session data collected during a current surgical session and provide the operation profile for use during the surgical session. As shown, system 400 may apply surgical session data 702 as an input to a pattern matching unit 704. Additionally, system 400 may be configured to access one or more distinct sets of operation pattern data 706 (e.g., operation pattern data 706-1, 706-2, to 706-N) representative of one or more distinct historical patterns of surgical procedure operations. System 400 may be configured to access the operation pattern data in any suitable way. For example, system 400 may be configured to access the operation pattern data in real time during the surgical session.

System 400 may apply operation pattern data 706 as inputs to pattern matching unit 704. Pattern matching unit 704 may compare surgical session data 702 with the one or more distinct sets of operation pattern data 706 to identify a distinct set of operation pattern data 706 representative of a first historical pattern of operations that is selected from among the one or more distinct historical patterns of surgical procedure operations and that matches the surgical session data 702. In the example of FIG. 7, pattern matching unit 704 identifies a distinct set of operation pattern data 706-2 representative of a first historical pattern of operations that best matches a first pattern represented by surgical session data 702.

Pattern matching unit 704 may perform any suitable heuristic, process, and/or operation that may be performed or executed by system 400 and that may be configured to identify a historical pattern (e.g., a distinct set of operation pattern data 706) that matches a collected pattern (e.g., a pattern identified in surgical session data 702). For example, pattern matching unit 704 may identify a distinct set of operation pattern data 706 that matches surgical session data 702 based on a comparison of attributes (e.g., force, velocity, acceleration, timing, trajectory of motion, etc.) of surgical session data 702 with the same attributes of historical operation pattern data 706. For instance, pattern matching unit 704 may find a match when values of one or more attributes of surgical session data 702 are within a predetermined tolerance (e.g., 5%) of the attribute values of a distinct set of operation pattern data 706. Additionally or alternatively, pattern matching unit 704 may implement a machine learning model configured to match surgical session data 702 with operation pattern data 706. Examples of how pattern matching unit 704 may identify a distinct historical pattern of operations that matches surgical session data 702 will be described below in more detail. It will be recognized that a "match" does not require an absolute match or a best match. Rather, the match may be any suitable correlation between a historical pattern and a collected surgical session data (e.g., a collected pattern), as may suit a particular implementation.

In some examples, pattern matching unit 704 may be implemented by hardware and/or software components (e.g., processors, memories, communication interfaces, instructions stored in memory for execution by the processors, etc.), such as storage facility 402 and/or processing facility 404 of system 400.

As mentioned, system 400 may be configured to provide, for use (e.g., by the computer-assisted surgical system) during the surgical session, an operation profile associated with the identified historical pattern (e.g., the distinct set of operation pattern data). For example, as shown in FIG. 7, each distinct set of operation pattern data 706 may be included in or associated with a distinct operation profile 708 (e.g., distinct operation profiles 708-1, 708-2, to 708-N), and each distinct operation profile 708 may include or be associated with one or more distinct sets of operation pattern data (e.g., distinct sets of operation pattern data 706-1, 706-2, 706-3, to 706-N). Accordingly, system 400 may provide, to the computer-assisted surgical system, operation profile 708-2, which includes or is associated with operation pattern data 706-2. System 400 may provide operation profile 708-2 to the surgical system in any suitable way, such as by accessing operation profile data representative of operation profile 708-2 and transmitting the operation profile data to the computer-assisted surgical system. Alternatively, system 400 may direct the computer-assisted surgical system to access the data directly from a source of the data (e.g., from remote computing system 502).

Operation profile 708-2 may be configured to be used by the computer-assisted surgical system during a surgical session in any suitable way. In some examples, operation profile 708-2 may be used by the computer-assisted surgical system to configure one or more system settings of the computer-assisted surgical system to adapt to particular preferences or habits of the user. Exemplary surgical system settings may include, but are not limited to, positional and/or ergonomic settings of a system component (e.g., a manipulator arm 112, master controls 204, eyepieces 212, armrest 216, etc.), endoscopic camera settings (e.g., exposure level, illumination intensity, output illumination color or wavelength), image display settings (e.g., a zoom level, a fluorescence image display color, a graphical user interface arrangement, etc.), and the like. In some aspects, operation profile 708-2 may include values of parameters associated with the system settings, and optionally may include instructions configured to direct the computer-assisted surgical system to set or adjust the values of the parameters.

Additionally or alternatively, operation profile 708-2 may be used by the computer-assisted surgical system to present information associated with a predicted event, e.g., an event that is likely to occur during the surgical session. To illustrate, operation pattern data 706-2 may indicate that a particular event (e.g., manipulator arm collisions) occurs frequently at certain times during surgical sessions when operations of a computer-assisted surgical session have a certain pattern. Accordingly, such operation pattern data 706-2 may be used to predict when such an event is likely to occur during a current surgical session having a similar operation pattern. Thus, an event may be predicted based on currently tracked surgical session data 702 and/or operation pattern data 706-2. In some examples, the event may be predicted by the computer-assisted surgical system (or by system 400) by comparing surgical session data 702 with operation profile 708-2. For instance, operation profile 708-2 may indicate that, upon the occurrence of a particular trigger event (e.g., fast movement of master controls with large trajectories), a particular response event (e.g., a collision of surgical instruments) is likely to occur.

The information associated with a predicted event may be provided by system 400 and/or by the computer-assisted surgical system. In some examples, information associated with a predicted event may include a notification (e.g., a displayed message, a warning tone, etc.) configured to notify a user that the predicted event is likely to occur, Additionally or alternatively, information associated with a predicted event may include user instructions for performing the predicted event or user instructions for avoiding an occurrence of the predicted event, as will be described below in more detail.

Operation profile 708-2 may include data representative of the information associated with a predicted event for presentation by the computer-assisted surgical system. The information may be in any suitable form, such as image content, video content, audio content (e.g., a warning tone, spoken instructions, etc.), and/or haptic feedback (e.g., vibration, etc.). The information may be presented in any suitable way, such as by way of display monitor 114, another computing device (e.g., a mobile device communicatively paired with surgical system 100), an audio speaker, etc.

In some examples, operation profile 708-2 may be configured to identify flaws and/or inefficiencies in user techniques and facilitate improvement of the user's techniques. Accordingly, operation profile 708-2 may include information configured to instruct a user to perform a particular operation differently. For instance, operation pattern data 706-2 may indicate that a suturing procedure is routinely performed with large loop trajectories of a suturing instrument. Accordingly, operation profile 708-2 may include information configured to instruct a user to perform a suturing procedure with smaller loop trajectories. Such information may be presented to the user by way of a notification (e.g., a message, an image, a video tutorial, audio instructions, etc.). The notification may be presented in any suitable way and at any suitable time. In some examples, the notification is presented in response to a determination that a suturing event is likely to occur, such as when surgical session data 702 indicates that a suturing instrument has been coupled to a manipulator arm 112.

Information associated with a predicted event may be added to operation profile 708-2 at any suitable time and in any suitable way, such as during a training session, during a video playback of the surgical procedure, in real time during a surgical session, and the like. In some embodiments, another user (e.g., a remote proctor monitoring the surgical session and/or training the surgeon, an assistant, etc.) may provide input (e.g., text input or audio input) explaining improvements in technique. The input may be provided by way of the computer-assisted surgical system (e.g., by user control system 104, display monitor 114, remote computing system 502, or any other computing system associated with surgical system 100). Additionally or alternatively, the other user may take control of the surgical instruments, such as by way of a second user control system, and demonstrate improved technique. Image, video, and/or audio data representative of the demonstration may then be stored to, or associated with, operation profile 708-2.

An operation profile has been described herein as including values of parameters associated with system settings, instructions configured to direct the computer-assisted surgical system to set or adjust the values of the parameters, and data representative of the information associated with a predicted event. However, an operation profile may include any other information or data that may be used as may suit a particular implementation. For example, an operation profile may include information describing or labeling certain events or operation pattern (e.g., excessive energy activation, excessive duration, anomalous, etc.). System 400 and/or the computer-assisted surgical system may present such information upon detection of an event associated with such information.

Examples of identifying, selecting, and using an operation profile will now be described. The following examples are merely illustrative and are not intended to be limiting in any way.

As a first example, system 400 may determine, based on a position of a surgeon's head as detected by head sensors included in viewer console 210, a proximity of the surgeon's head to viewer console 210. System 400 may identify, from among operation pattern data 706-1, 706-2, to 706-N, operation pattern data 706-2 representative of a distinct historical pattern of operations that matches surgical session data 702, including data representative of the determined proximity of the surgeon's head to viewer console 210. System 400 may then provide to surgical system 100 operation profile 708-2 associated with operation pattern data 706-2. Operation profile 708-2 may specify a position for master controls 204 and head sensor and eye sensor sensitivity levels, optimized for a person positioned with the particular proximity to viewer console 210. User control system 200 may then use the operation profile to automatically adjust the position of master controls 204 and the sensitivity settings of the head sensors and eye sensors to the position and levels specified in the operation profile. In this way, operation profile 708-2 may be used by surgical system 100 to automatically customize an ergonomic and positional setting of master controls 204 and system settings (sensor sensitivity levels) based on the surgeon's indirect user interactions with surgical system 100, and without knowing an identity of the surgeon.

As another example, an inexperienced assistant (e.g., assistant 110-2) may have difficulty positioning manipulator arms 112 in a proper position for a surgical procedure. System 400 may identify, based on tracked direct user interactions with manipulator arms 112 and user input devices 316 (e.g., a port clutch button and an instrument clutch button), operation pattern data 706-2 representative of a distinct historical pattern of operations that matches surgical session data 702. System 400 may then provide to surgical system 100 operation profile 708-2 associated with operation pattern data 706-2. Operation profile 708-2 may specify preferred positions for manipulator arms 112, and may display on display monitor 114 image and/or video content showing the correct positions of manipulator arms 112. Additionally or alternatively, if manipulator arms 112 are mechanized, operation profile 708-2 may include data representative of instructions configured to direct an automatic adjustment of the position of manipulator arms 112 to the specified position during a targeting operation. In these ways, operation profile 708-2 may be used by the computer-assisted surgical system to facilitate positioning of manipulator arms 112 based on direct user interactions with the computer-assisted surgical system, and without knowing the identity of the assistant.

Figure 8:
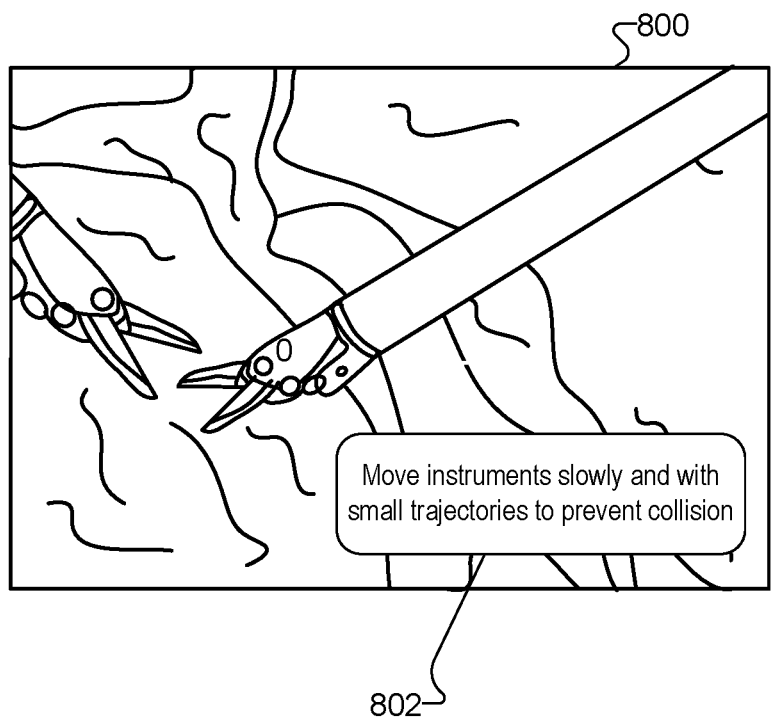
FIG. 8 illustrates an exemplary notification that may be generated based on a selected operation profile and presented by a computer-assisted surgical system according to principles described herein.

As another example, operation profile 708-2 may indicate that surgical instruments located within a predetermined proximity of one another are likely to collide due to fast movement and large trajectories of master controls 204 that are common with operation profile 708-2. Accordingly, operation profile 708-2 may include data representative of a warning message to be presented to the user. FIG. 8 illustrates an exemplary notification that may be presented to the user, FIG. 8 illustrates an image 800 presented by way of an image display system included in a user control system (e.g., image display system 208 included in user control system 200). Image 800 includes a message 802 superimposed on a view of the surgical area. As shown, message 802 states: "Move instruments slowly and with small trajectories to prevent collision." It will be appreciated that message 802 may be positioned at any location and may provide any information as may suit a particular implementation.

Referring again to FIG. 7, in some examples, the computer-assisted surgical session may use operation profile 708-2 to facilitate login and/or authentication of a user. For example, operation profile 708-2 may be associated with, or included in, a user profile for a particular user. As an example, operation profile 708-2 may include identification information for a distinct user (e.g., the user's name, surgical team role, login credentials, etc.). Accordingly, upon identification of operation pattern data 706-2 that matches surgical session data 702 (e.g., data representative button presses and foot pedal presses), system 400 may determine that the distinct user associated with operation profile is interacting with surgical system 100. Accordingly, system 400 may automatically login and/or authenticate the user. In some examples, the user may be authenticated without the computer-assisted surgical system receiving, from the user, any user credentials (e.g., username, password, biometric identification, etc.). With the systems and methods described herein, a user can be automatically logged in and/or authenticated by interacting with any computer-assisted surgical system that has access to the operation profile associated with the user. In other words, the user's distinct patterns of interacting with one or more computer-assisted surgical systems can be used across different computer-assisted surgical systems, different models, etc., to authenticate and/or log in the user.

In some examples, the automatic login and/or authentication may be performed only when system 400 has identified the distinct user with a certainty greater than or equal to a predetermined threshold value (e.g., 99% certainty). The certainty value may be scored in any suitable way and with any suitable algorithm.

In some examples, such as when the certainty value is less than the particular threshold value, system 400 may identify one or more users that are likely to be interacting with surgical system 100 and require the user to provide confirmation of the current user's identity prior to login and/or authentication of the user. For instance, system 400 may determine with 75% certainty that operation pattern data 706-2 indicates that a first surgeon is interacting with surgical system 100, and may determine with approximately 25% certainty that operation pattern data 706-2 indicates that a second surgeon is interacting with surgical system 100. Accordingly, touchscreen display 218 may present a graphical user interface that prompts the user to select either the first surgeon or the second surgeon, after which system 400 may login and/or authenticate the selected user.

Upon login and/or authentication of the user, surgical session data 702 may be added to, or used to update, operation pattern data 706-2 and/or operation profile 708-2. Additionally or alternatively, upon authentication of the user, certain features may be enabled or unlocked for the user. For example, the user may be allowed to customize various system settings and set personal preferences.

The systems and methods described above include identifying a distinct historical pattern that matches a collected pattern from the collected surgical session data and providing a distinct operation profile for use during a surgical session. However, the systems and methods are not limited to identifying a single distinct historical pattern or providing a single, distinct operation profile for use during the surgical session.

Figure 9:
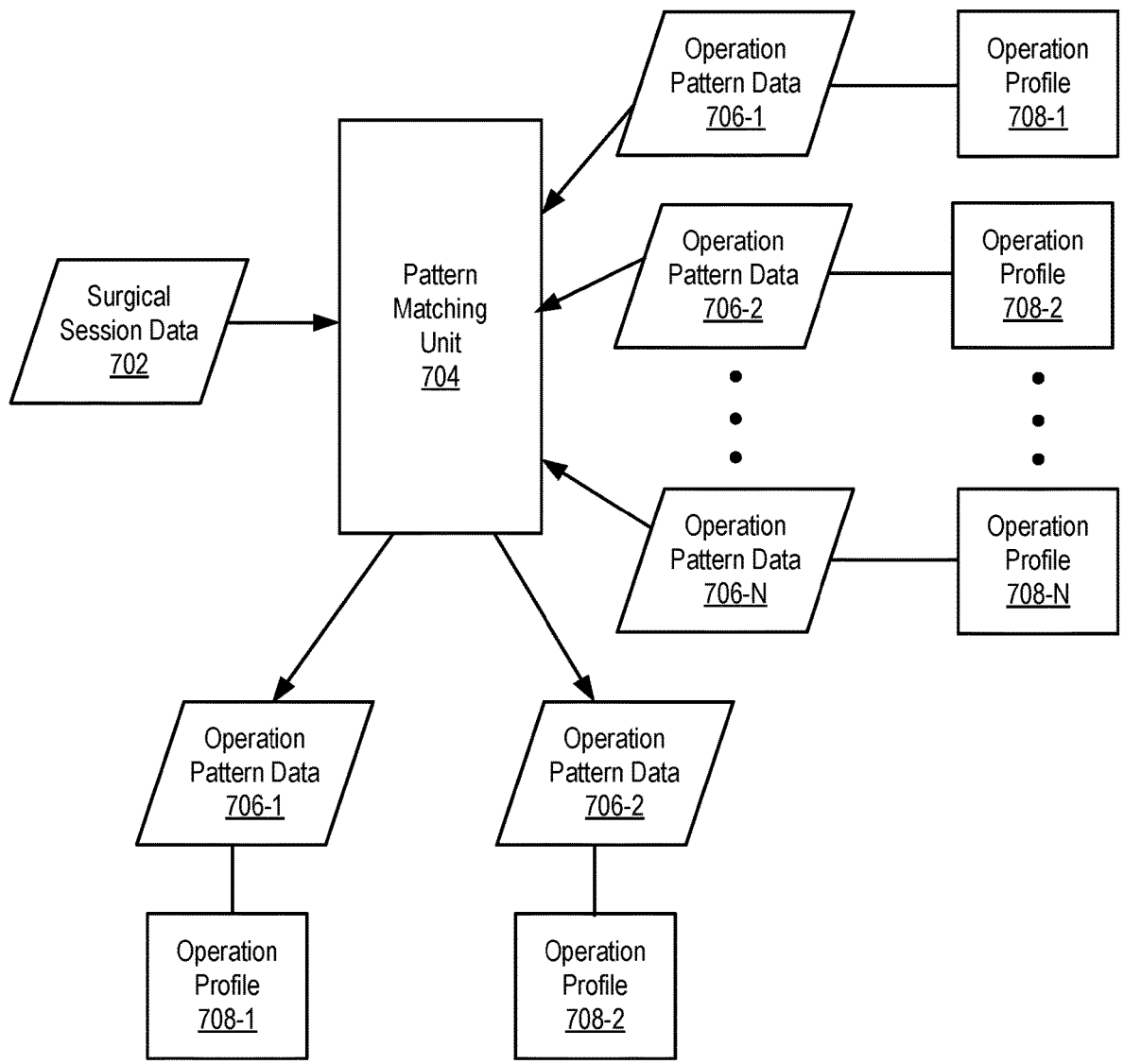
FIG. 9 illustrates an exemplary identification of a plurality of distinct sets of operation pattern data based on surgical session data and selection of a plurality of operation profiles according to principles described herein.

In some examples, system 400 may identify multiple historical patterns (e.g., distinct sets of operation pattern data) that match currently collected surgical session data. FIG. 9 illustrates another exemplary manner in which system 400 may select multiple operation profiles based on surgical session data and provide the operation profiles to the computer-assisted surgical system. FIG. 9 is similar to FIG. 7 except that pattern matching unit 704 identifies two historical patterns (e.g., operation pattern data 706-1 and 706-2) that match distinct collected patterns (subsets of surgical session data 702), and provides two distinct operation profiles 708 (operation profiles 708-1 and 708-2) to the computer-assisted surgical system. While FIG. 9 illustrates two distinct sets of operation pattern data 706 and two operation profiles 708, pattern matching unit 704 may identify any number of distinct sets of operation pattern data 706 that match surgical session data and may provide any number of operation profiles 708 to the surgical system, as may suit a particular implementation.

In the example illustrated in FIG. 9, surgical session data 702 may be representative of multiple distinct patterns of operations (collected patterns). For example, surgical session data 702 may be representative of operations based on interactions by a first user (e.g., surgeon 110-1) during the surgical session and operations based on user interactions by a second user (e.g., assistant 110-2) during the surgical session. Accordingly, pattern matching unit 704 may identify operation pattern data 706-1 as matching a distinct subset of surgical session data 702 associated with a first distinct pattern of operation (e.g., operations by the first user) and operation pattern data 706-2 as matching another distinct subset of surgical session data 702 associated with a second distinct pattern of operations (e.g., operations by the second user). System 400 may then provide, to the computer-assisted surgical system, operation profile 708-1, which may be configured to customize system settings and provide notifications for the first user, and operation profile 708-2, which may be configured to customize system settings and provide notifications for the second user.

As an alternative example, surgical session data 702 may be representative of operations based on interactions by a single user at different times, such as during different stages of a surgical session (e.g., a tissue ablation stage and a suturing stage). Accordingly, pattern matching unit 704 may identify operation pattern data 706-1 as matching a distinct subset of surgical session data 702 generated during a first time period of the surgical session and operation pattern data 706-2 as matching a distinct subset of surgical session data 702 associated with a second time period of the surgical session. System 400 may then provide, to the computer-assisted surgical system; operation profile 708-1, which may be configured to customize system settings and provide notifications for the first time period of the surgical session, and operation profile 708-2, which may be configured to customize system settings and provide notifications for the second time period of the surgical session.

As a further example, operation profile 708-1 may be configured to customize a first set of system settings (e.g., ergonomic settings) and operation profile 708-2 may be configured to customize a second set of system settings (e.g., camera and image display settings).

In some examples, system 400 may implement a machine learning model configured to classify or generate an operation pattern of a computer-assisted surgical system based on surgical session data generated during a current surgical session. A classified operation pattern may then be used by system 400 to select and provide an operation profile to the computer-assisted surgical system for use during the surgical session. Any suitable machine learning model may be implemented by system 400, examples of which will now be described.

Figure 10:
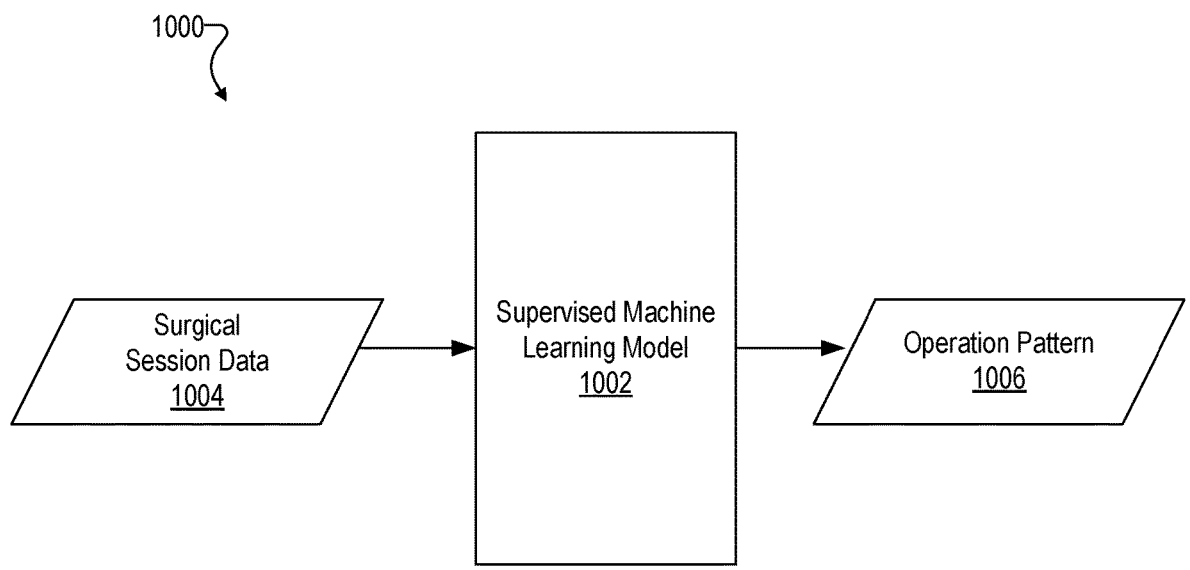
FIG. 10 illustrates an exemplary configuration in which a supervised machine learning model is maintained or otherwise accessed by the exemplary operation profile system of FIG. 4 according to principles described herein.

FIG. 10 illustrates an exemplary configuration 1000 in which a supervised machine learning model 1002 is maintained or otherwise accessed by system 400. Supervised machine learning model 1002 is supervised in that it is specifically trained with pre-classified data prior to being used by system 400 to identify and classify one or more operation patterns in surgical session data.

Supervised machine learning model 1002 may be maintained by system 400 itself (e.g., by storage facility 402), Alternatively, supervised machine learning model 1002 may be maintained by a system remote from system 400 and accessed by system 400 (e.g., by way of a network).

As shown, supervised machine learning model 1002 receives surgical session data 1004 as input. Surgical session data 1004 may represent operations of a computer-assisted surgical system, and may include, for example, interaction event data and/or response event data.

Supervised machine learning model 1002 may analyze surgical session data 1004 in any suitable manner. For example, supervised machine learning model 1002 may analyze surgical session data 1004 in accordance with one or more decision tree learning algorithms, association rule learning algorithms, artificial neural network learning algorithms, deep learning algorithms, bitmap algorithms, and/or any other suitable data analysis technique as may serve a particular implementation.

In some examples, supervised machine learning model 1002 is configured to identify and classify a distinct operation pattern 1006 based on the user interaction events and/or response events represented by surgical session data 1004 (e.g., interaction event data and response event data). Operation pattern 1006 may be indicative of a distinct pattern of operations of the computer-assisted surgical system. For the example, operation pattern 1006 may indicate a pattern in how user input devices (e.g., foot pedals, buttons, touchscreen displays, master controls, etc.) are actuated (e.g., force, duration, timing, etc.), a pattern in how system components (e.g., master controls 204, manipulator arms 112, surgical instruments coupled to manipulator arms 112, etc.) are moved (e.g., trajectories, force, velocity, acceleration, timing, etc.), a pattern in how system settings are configured (e.g., values of ergonomic settings, camera settings, image display settings, etc.), and the like. System 400 may then select an operation profile associated with the classified operation pattern 1006 and provide the selected operation profile to the computer-assisted surgical system for use during the surgical session, as described herein.

Supervised machine learning model 1002 may be trained in any suitable manner. For example, supervised machine learning model 1002 may implement a machine learning classifier (e.g., a random forest classifier) and may be trained by providing interaction event data and/or response event data of a known operation pattern as training inputs to supervised machine learning model 1002. For instance, a set of labeled training data may be in the form:

$$[f1(i,t), f2(i,t), \ldots, fN(i,t), O(i,t)]$$

where:
- "i" is an index representing a particular historical surgical session,
- "t" is an index representing a time segment within the particular surgical session,
- f1(i,t), f2(i,t), ... fN(i,t) are feature values for one or more tracked interaction events and/or response events for the time segment within the particular surgical session (e.g., average duration of pressing foot pedal 206-1), and
- O(i,t) is an identifier of the operation pattern.

Alternatively, supervised machine learning model 1002 may implement a neural network or deep learning model (e.g., long short-term memory) and may be trained by providing as input a labeled set of time-series data along with the operator identifier. The time-series data may include, for example, a sequence of foot pedal 206-2 ON/OFF presses, a sequence of user input devices 316 (e.g., port clutch and instrument clutch buttons) ON/OFF presses, etc.

Once supervised machine learning model 1002 is trained, an unlabeled input vector (e.g., surgical session data 1004 generated during a current surgical session) can be provided as input, and supervised machine learning model 1002 may return a set of predicted operation patterns (e.g., operation pattern data 706-1: 98% probability; operation pattern data 706-2: 1.5% probability). In some examples, system 400 may select a predicted operation pattern if its probability is equal to or greater than a predetermined threshold value (e.g., 95%) and provide to the computer-assisted surgical system an operation profile associated with the selected operation pattern. Additionally, if all predicted operation pattern are less than the predetermined threshold value, system 400 may generate a new set of operation pattern data and a new operation profile.

The training of supervised machine learning model 1002 may be performed prior to system 400 using supervised machine learning model 1002 to classify an operation pattern based surgical session data 1004. Additionally or alternatively, supervised machine learning model 1002 may be trained while system 400 is using supervised machine learning model 1002 to classify an operation pattern. For example, in response to an operation pattern classification during a surgical session, system 400 may provide a notification to a user (e.g., to surgeon 110-1 or another surgical team member 110). The user may provide user input (e.g., by selecting an option included in the notification) confirming or refuting the operation pattern classification and/or the selected operation profile, System 400 may receive the user input and provide the user input as a training input to supervised machine learning model 1002.

In the foregoing description, system 400 has been described as implementing a supervised learning model to classify an operation pattern of a computer-assisted surgical system. However, system 400 may additionally or alternatively implement an unsupervised machine learning model, as may suit a particular implementation. In some examples, distinct sets of operation pattern data and distinct operation profiles associated with the operation pattern data may be generated by an unsupervised machine learning model, such as by use of a clustering algorithm. Additionally, an unsupervised machine learning model may be configured to cluster surgical session data into a plurality of distinct sets of operation pattern data each representative of a distinct pattern of operations of the computer-assisted surgical system during a current surgical session. The distinct sets of operation pattern data may be based on, for example, different users (e.g., surgeon 110-1 and assistant 110-2), different features of the computer-assisted surgical system (e.g., endoscopic camera features, surgical instrument features, ergonomic settings, etc.), different times or stages of the surgical session, and the like.

Figure 11:
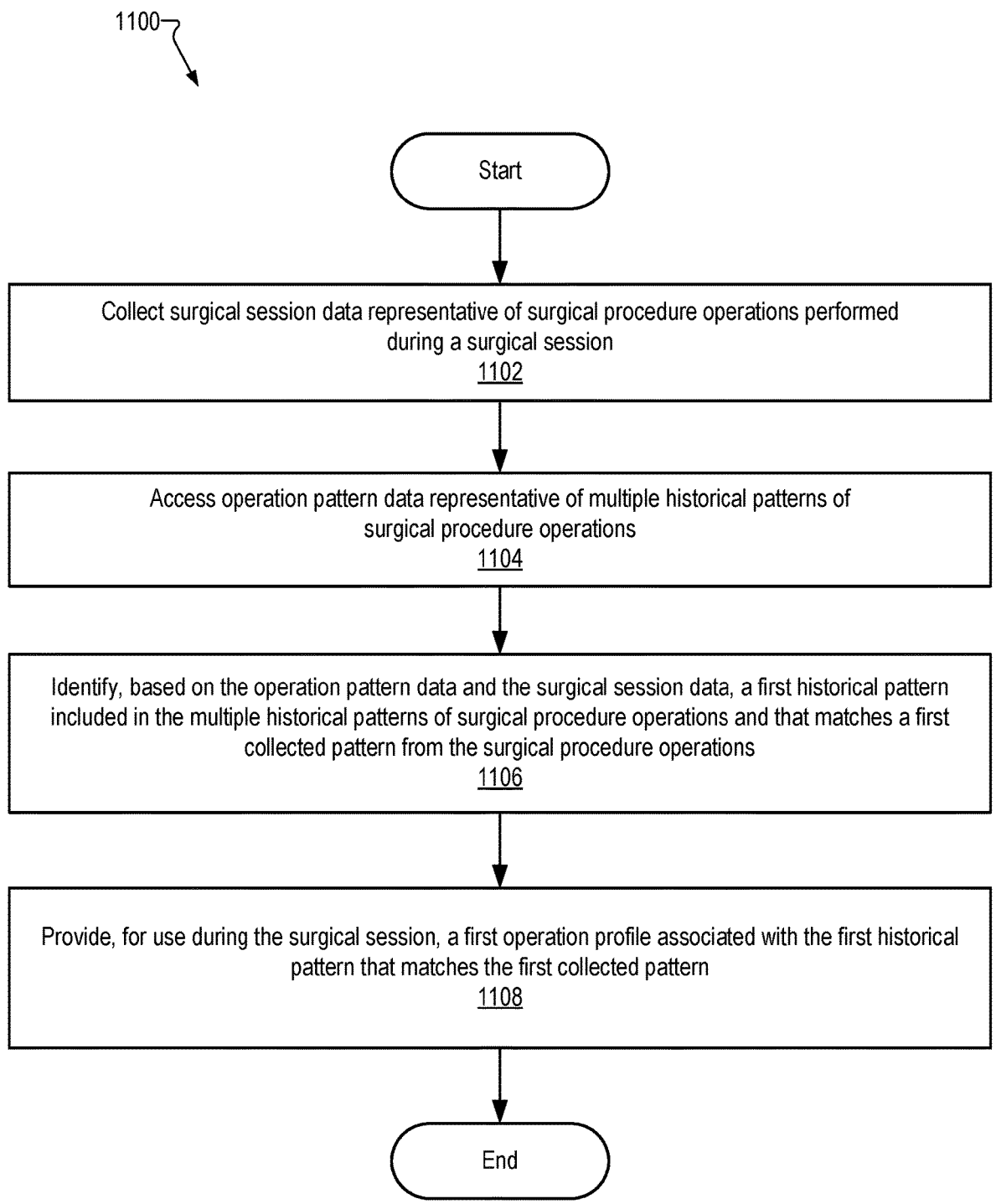
FIG. 11 illustrates an exemplary method of identifying a distinct set of operation pattern data for a current surgical session and providing an associated operation profile to a computer-assisted surgical session for use during the surgical session according to principles described herein.

FIG. 11 illustrates an exemplary method 1100. While FIG. 11 illustrates exemplary operations according to one embodiment, other embodiments may omit, add to, reorder, and/or modify any of the operations shown in FIG. 11. One or more of the operations shown in FIG. 11 may be performed by system 400, any components included therein, and/or any implementation thereof.

In operation 1102, an operation profile system collects surgical session data representative of surgical procedure operations performed during a surgical session. Operation 1102 may be performed in any of the ways described herein.

In operation 1104, the operation profile system accesses operation pattern data representative of multiple historical patterns of surgical procedure operations. Operation 1104 may be performed in any of the ways described herein.

In operation 1106, the operation profile system identifies, based on the operation pattern data and the surgical session data, a first historical pattern included in the multiple historical patterns of surgical procedure operations and that matches a first collected pattern from the surgical procedure operations. Operation 1106 may be performed in any of the ways described herein.

In operation 1108, the operation profile system provides, for use during the surgical session, a first operation profile associated with the first historical pattern that matches the first collected pattern. Operation 1108 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 12:
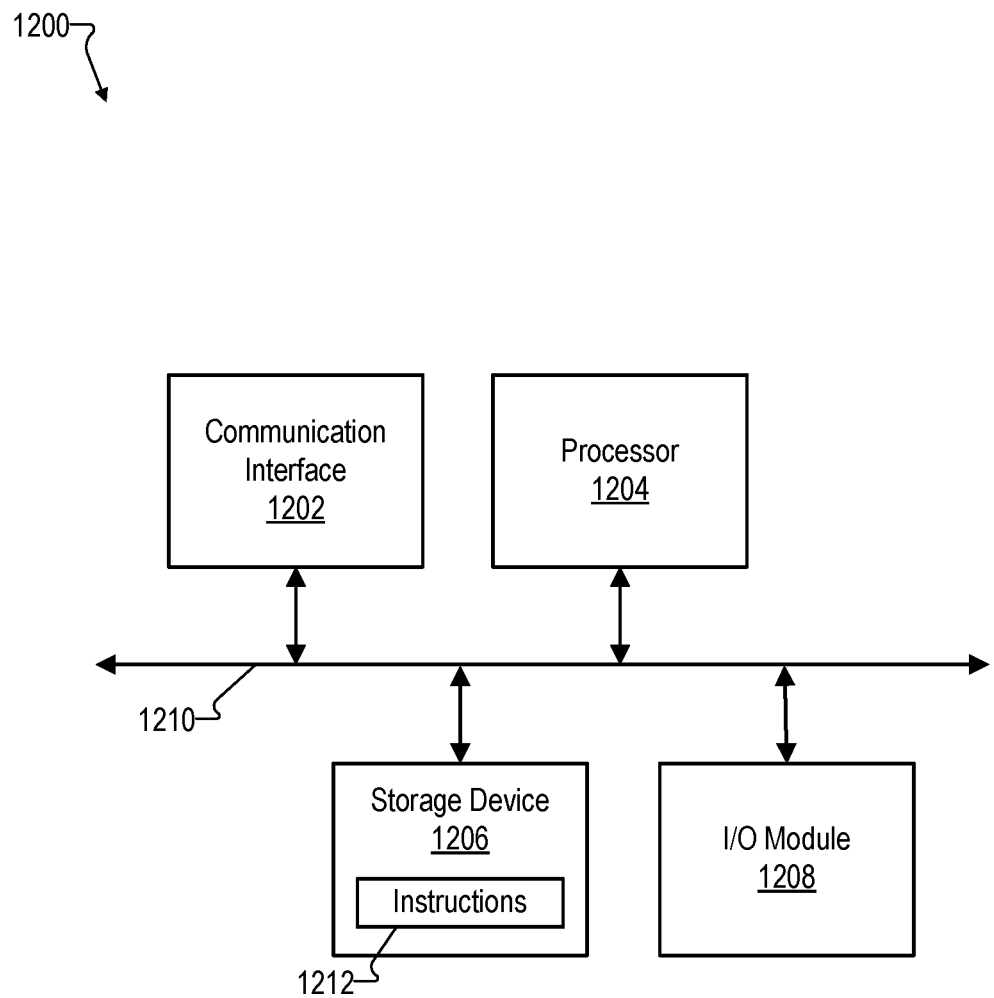
FIG. 12 illustrates an exemplary computing system according to principles described herein.

FIG. 12 illustrates an exemplary computing device 1200 that may be specifically configured to perform one or more of the processes described herein. As shown in FIG. 12, computing device 1200 may include a communication interface 1202, a processor 1204, a storage device 1206, and an input/output ("I/O") module 1208 communicatively connected one to another via a communication infrastructure 1210. While an exemplary computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data and/or interpreting, executing, and/or directing execution of one or more of the instructions, processes, and/or operations described herein. Processor 1204 may perform operations by executing computer-executable instructions 1212 (e.g., an application, software, code, and/or other executable data instance) stored in storage device 1206.

Storage device 1206 may include one or more data storage media, devices, or configurations and may employ any type, form, and combination of data storage media and/or device. For example, storage device 1206 may include, but is not limited to, any combination of the non-volatile media and/or volatile media described herein.

Electronic data, including data described herein, may be temporarily and/or permanently stored in storage device 1206. For example, data representative of computer-executable instructions 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. One or more I/O modules may be used to receive input for a single virtual experience. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or IR receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the systems, computing devices, and/or other components described herein may be implemented by computing device 1200. For example, processing facility 404 may be implemented by processor 1204 and storage facility 402 may be implemented by storage device 1206.

In the preceding description, various exemplary embodiments have been described with reference to the accompanying drawings. It will, however, be evident that various modifications and changes may be made thereto, and additional embodiments may be implemented, without departing from the scope of the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
collect, during a surgical session performed with a computer-assisted surgical system, surgical session data representative of surgical procedure operations performed during the surgical session, wherein:
the computer-assisted surgical system includes a manipulating system and a user control system,
the manipulating system includes a manipulator arm configured to couple with a surgical instrument,
the user control system controls at least one of the manipulator arm or the surgical instrument based on user input, and
the surgical procedure operations include at least one of user interaction events or response events, the user interaction events comprising distinct interactions by one or more users with the computer-assisted surgical system during the surgical session and the response events comprising distinct operations performed during the surgical session and by the computer-assisted surgical system in response to interaction events;

access, during the surgical session, operation pattern data representative of multiple historical patterns of surgical procedure operations;

identify, during the surgical session and based on the operation pattern data and the surgical session data, a first historical pattern included in the multiple historical patterns of surgical procedure operations and that matches a first collected pattern from the surgical procedure operations;

identify, during the surgical session, a first operation profile associated with the first historical pattern that matches the first collected pattern; and configure, during the surgical session based on information included in the first operation profile, a system setting of the computer-assisted surgical system.

2. The system of claim 1, wherein:
the processor is further configured to execute the instructions to identify, based on the operation pattern data and the surgical session data, a second historical pattern included in the multiple historical patterns of surgical procedure operations and that matches a second collected pattern from the surgical procedure operations,
the operation profile is associated with the second historical pattern, and
the operation profile is provided for use during the surgical session in response to the identification of either the first historical pattern or the second historical pattern.

3. The system of claim 1, wherein:
the processor is further configured to execute the instructions to identify, based on the operation pattern data and the surgical session data, a second historical pattern included in the multiple historical patterns of surgical procedure operations and that matches a second collected pattern from the surgical procedure operations,
the operation profile is associated with the second historical pattern, and
the operation profile is only provided for use during the surgical session in response to the identification of both the first historical pattern and the second historical pattern.

4. The system of claim 1, wherein:
the surgical procedure operations include an interaction event, and
the surgical session data includes interaction event data representative of the interaction event, the interaction event data indicating one or more of a force, a velocity, an acceleration, a pose, a state, and a timing of the interaction event.

5. The system of claim 1, wherein:
the surgical procedure operations include a response event, and
the surgical session data includes response event data representative of the response event.

6. The system of claim 1, wherein the processor is further configured to:
determine, based on the operation profile, that a particular response event is likely to occur during the surgical session, and direct, in response to the determination that the particular response event is likely to occur, the computer-assisted surgical system to provide, during the surgical session, information associated with the particular response event.

7. The system of claim 1, wherein:
the operation profile is associated with a user profile, and
the processor is further configured to identify, based on the user profile, an identity of the user.

8. The system of claim 1, wherein:
the processor is further configured to
identify, based on the operation pattern data and the surgical session data, a second historical pattern included in the multiple historical patterns of surgical procedure operations and that matches a second collected pattern from the surgical procedure operations, and
provide, for use during the surgical session, a second operation profile associated with the second historical pattern that matches the second collected pattern,
the first historical pattern is identified based on a first subset of the operation pattern data, and
the second historical pattern is identified based on a second subset of the operation pattern data and that is different from the first subset of the operation pattern data.

9. A method comprising:
collecting, by an operation profile system during a surgical session performed with a computer-assisted surgical system, surgical session data representative of surgical procedure operations performed during the surgical session, wherein:
the computer-assisted surgical system includes a manipulating system and a user control system,
the manipulating system includes a manipulator arm configured to couple with a surgical instrument,
the user control system controls at least one of the manipulator arm or the surgical instrument based on user input, and
the surgical procedure operations include at least one of user interaction events or response events, the user interaction events comprising distinct interactions by one or more users with the computer-assisted surgical system during the surgical session and the response events comprising distinct operations performed during the surgical session and by the computer-assisted surgical system in response to interaction events;

accessing, by the operation profile system during the surgical session, operation pattern data representative of multiple historical patterns of surgical procedure operations;

identifying, by the operation profile system during the surgical session and based on the operation pattern data and the surgical session data, a first historical pattern included in the multiple historical patterns of surgical procedure operations and that matches a first collected pattern from the surgical procedure operations;

identifying, by the operation profile system during the surgical session, a first operation profile associated with the first historical pattern that matches the first collected pattern; and configuring, during the surgical session based on information included in the first operation profile, a system setting of the computer-assisted surgical system.

10. The method of claim 9, further comprising:
identifying, by the operation profile system based on the operation pattern data and the surgical session data, a second historical pattern included in the multiple historical patterns of surgical procedure operations and that matches a second collected pattern from the surgical procedure operations,
wherein:
  the operation profile is associated with the second historical pattern, and
  the operation profile is provided for use during the surgical session in response to the identification of either the first historical pattern or the second historical pattern.

11. The method of claim 9, further comprising:
identifying, by the operation profile system based on the operation pattern data and the surgical session data, a second historical pattern included in the multiple historical patterns of surgical procedure operations and that matches a second collected pattern from the surgical procedure operations,
wherein:
  the operation profile is associated with the second historical pattern, and
  the operation profile is only provided for use during the surgical session in response to the identification of both the first historical pattern and the second historical pattern.

12. The method of claim 9, wherein
the surgical procedure operations include an interaction event, and
the surgical session data includes interaction event data representative of the interaction event, the interaction event data indicating one or more of a force, a velocity, an acceleration, a pose, a state, and a timing of the interaction event.

13. The method of claim 9, wherein
the surgical procedure operations include a response event, and
the surgical session data includes response event data representative of the response event.

14. The method of claim 9, further comprising:
determining, by the operation profile system based on the operation profile, that a particular response event is likely to occur during the surgical session, and
directing, by the operation profile system in response to the determining that the particular response event is likely to occur, the computer-assisted surgical system to provide, during the surgical session, information associated with the particular response event.

15. The method of claim 9, wherein
the operation profile is associated with a user profile, and the method further comprises identifying, based on the user profile, an identity of the user.

16. A non-transitory computer-readable medium storing instructions that, when executed, direct at least one processor of a computing device to:
  collect, during a surgical session performed with a computer-assisted surgical system, surgical session data representative of surgical procedure operations performed during the surgical session, wherein:
    the computer-assisted surgical system includes a manipulating system and a user control system,
    the manipulating system includes a manipulator arm configured to couple with a surgical instrument,
    the user control system controls at least one of the manipulator arm or the surgical instrument based on user input, and
    the surgical procedure operations include at least one of user interaction events or response events, the user interaction events comprising distinct interactions by one or more users with the computer-assisted surgical system during the surgical session and the response events comprising distinct operations performed during the surgical session and by the computer-assisted surgical system in response to interaction events;
  access, during the surgical session, operation pattern data representative of multiple historical patterns of surgical procedure operations;
  identify, during the surgical session and based on the operation pattern data and the surgical session data, a first historical pattern included in the multiple historical patterns of surgical procedure operations and that matches a first collected pattern from the surgical procedure operations;
  identify, during the surgical session, a first operation profile associated with the first historical pattern that matches the first collected pattern; and
  configure, during the surgical session based on information included in the first operation profile, a system setting of the computer-assisted surgical system.

17. The computer-readable medium of claim 16, wherein:
the medium further stores instructions that, when executed, further direct the at least one processor of the computing device to identify, based on the operation pattern data and the surgical session data, a second historical pattern included in the multiple historical patterns of surgical procedure operations and that matches a second collected pattern from the surgical procedure operations,
the operation profile is associated with the second historical pattern, and
the operation profile is provided for use during the surgical session in response to the identification of either the first historical pattern or the second historical pattern.

18. The computer-readable medium of claim 16, wherein:
the medium further stores instructions that, when executed, further direct the at least one processor of the computing device to identify, based on the operation pattern data and the surgical session data, a second historical pattern included in the multiple historical patterns of surgical procedure operations and that matches a second collected pattern from the surgical procedure operations,
the operation profile is associated with the second historical pattern, and
the operation profile is only provided for use during the surgical session in response to the identification of both the first historical pattern and the second historical pattern.

19. The system of claim 1, wherein the system setting comprises a positional setting or an ergonomic setting of a component of the computer-assisted surgical system.

20. The system of claim 1, wherein the system setting comprises a setting of an imaging device included in the computer-assisted surgical system or a setting of an image display system included in the computer-assisted surgical system.

\* \* \* \* \*